United States Patent
Pearson et al.

(10) Patent No.: US 8,251,056 B2
(45) Date of Patent: Aug. 28, 2012

(54) INHALER

(75) Inventors: Allen John Pearson, Huntingdon (GB); Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 903 days.

(21) Appl. No.: 12/066,048

(22) PCT Filed: Sep. 7, 2006

(86) PCT No.: PCT/GB2006/003307
§ 371 (c)(1), (2), (4) Date: Mar. 6, 2008

(87) PCT Pub. No.: WO2007/028992
PCT Pub. Date: Mar. 15, 2007

(65) Prior Publication Data
US 2009/0229604 A1    Sep. 17, 2009

(30) Foreign Application Priority Data
Sep. 8, 2005 (GB) .................................. 0518355.3

(51) Int. Cl.
*A61M 11/00* (2006.01)
*B65D 83/00* (2006.01)

(52) U.S. Cl. ......... 128/200.23; 128/200.14; 222/402.11; 222/402.12; 222/402.2

(58) Field of Classification Search ................ 128/200.14–200.23; 222/402.2, 222/402.11, 402.12, 153.11, 153.13–153.14
See application file for complete search history.

(56) References Cited

U.S. PATENT DOCUMENTS

| 4,664,107 A | 5/1987 | Wass |
| 4,771,769 A | 9/1988 | Hegemann et al. |
| 4,860,738 A | 8/1989 | Hegemann et al. |
| 4,944,429 A | 7/1990 | Bishop et al. |
| 4,969,578 A | 11/1990 | Gander et al. |
| 5,069,204 A | 12/1991 | Smith et al. |
| 5,119,806 A * | 6/1992 | Palson et al. ............ 128/200.14 |
| 5,447,150 A | 9/1995 | Bacon |
| 5,826,571 A | 10/1998 | Casper et al. |
| 5,860,416 A | 1/1999 | Howlett |
| 5,896,853 A | 4/1999 | Howlett |
| 5,899,200 A | 5/1999 | McNary |
| 6,062,214 A * | 5/2000 | Howlett .................. 128/200.23 |
| 6,261,274 B1 | 7/2001 | Arghyris et al. |
| 6,302,101 B1 | 10/2001 | Py |
| 6,354,290 B1 | 3/2002 | Howlett |

(Continued)

FOREIGN PATENT DOCUMENTS
EP    0075548 A2    3/1983
(Continued)

*Primary Examiner* — Steven Douglas
*Assistant Examiner* — Rachel Young
(74) *Attorney, Agent, or Firm* — James P. Riek

(57) ABSTRACT

An inhaler is provided with a closure which may be moved between a closed and open position in order to cover and uncover a mouthpiece. The closure is associated with a revolvable element including a restricting member. Movement of the closure from the open position to the closed position causes the revolvable element to revolve around an axis X thereby placing the restricting member in a restricting position which restricts relative movement between a container unit and the housing such that unintentional actuation of the inhaler is prevented. The inhaler is useful, for example, in the treatment of asthma.

48 Claims, 17 Drawing Sheets

U.S. PATENT DOCUMENTS

| | | | |
|---|---|---|---|
| 6,364,166 B1 | 4/2002 | Ritsche et al. | |
| 6,484,715 B1 | 11/2002 | Ritsche et al. | |
| 6,578,741 B2 | 6/2003 | Ritsche et al. | |
| 6,637,432 B2 | 10/2003 | Wakefield et al. | |
| 6,644,305 B2 | 11/2003 | MacRae et al. | |
| 6,701,917 B2 | 3/2004 | O'Leary | |
| 6,718,972 B2 | 4/2004 | O'Leary | |
| 6,729,324 B2 | 5/2004 | Casper et al. | |
| 6,792,941 B2 | 9/2004 | Andersson | |
| 2002/0056449 A1* | 5/2002 | Wakefield et al. | 128/200.23 |
| 2002/0117513 A1 | 8/2002 | Helmlinger | |
| 2003/0052196 A1 | 3/2003 | Fuchs | |
| 2003/0100867 A1 | 5/2003 | Fuchs | |
| 2004/0069301 A1* | 4/2004 | Bacon | 128/200.23 |
| 2004/0237961 A1* | 12/2004 | Snow et al. | 128/200.23 |
| 2005/0011515 A1* | 1/2005 | Lee et al. | 128/200.23 |

FOREIGN PATENT DOCUMENTS

| | | | |
|---|---|---|---|
| EP | 0414536 | A2 | 2/1991 |
| EP | 0428380 | A1 | 5/1991 |
| EP | 1066075 | B1 | 1/2001 |
| FR | 2682305 | | 4/1993 |
| GB | 2263873 | A | 8/1993 |
| GB | 2264238 | A | 8/1993 |
| GB | 2272162 | A | 5/1994 |
| GB | 2364320 | A | 1/2002 |
| GB | 2398252 | A | 8/2004 |
| GB | 2419292 | A | 4/2006 |
| WO | 9852634 | A1 | 11/1998 |
| WO | 0170314 | A1 | 9/2001 |
| WO | 0187391 | A2 | 11/2001 |
| WO | 0249698 | A1 | 6/2002 |
| WO | 03026803 | A1 | 4/2003 |
| WO | 03026804 | A1 | 4/2003 |
| WO | 03026805 | A1 | 4/2003 |
| WO | 03029105 | A1 | 4/2003 |
| WO | 03043909 | A2 | 5/2003 |
| WO | 03061843 | A1 | 7/2003 |
| WO | 03074189 | A1 | 9/2003 |
| WO | 03080161 | A1 | 10/2003 |
| WO | 03095006 | A2 | 11/2003 |
| WO | 03095007 | A2 | 11/2003 |
| WO | 2004028608 | A1 | 4/2004 |
| WO | 2004041334 | A2 | 5/2004 |
| WO | 2004041339 | A2 | 5/2004 |
| WO | 2004073776 | A1 | 9/2004 |
| WO | 2004096329 | A1 | 11/2004 |
| WO | 2005046774 | A1 | 5/2005 |
| WO | 2005087299 | A1 | 9/2005 |
| WO | 2005107838 | A1 | 11/2005 |
| WO | 2005107955 | A1 | 11/2005 |
| WO | 2005110520 | A1 | 11/2005 |
| WO | 2006087385 | A1 | 8/2006 |
| WO | 2006097756 | | 9/2006 |

* cited by examiner

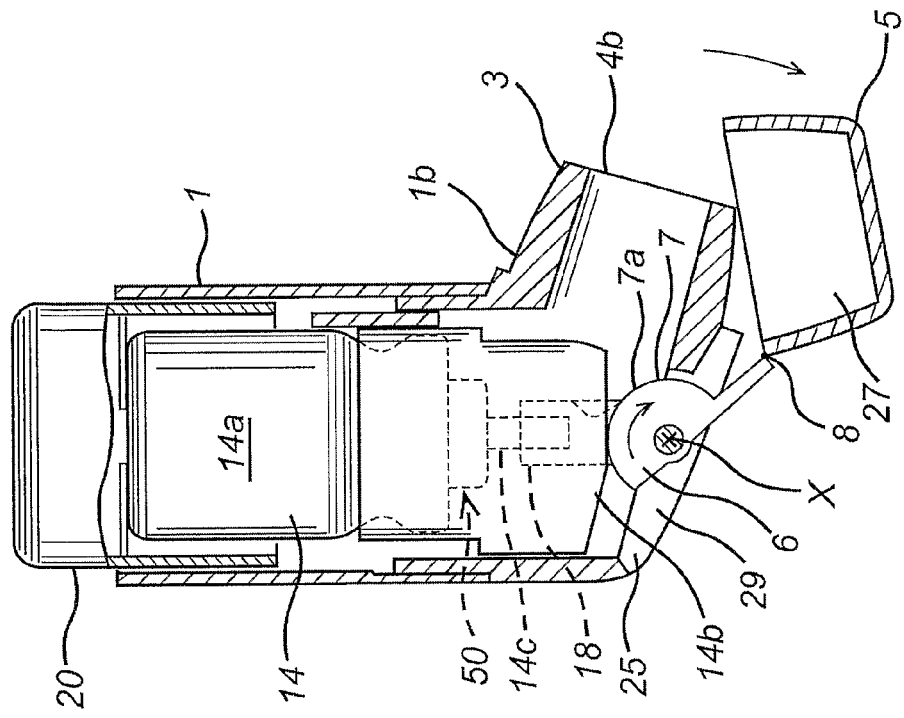
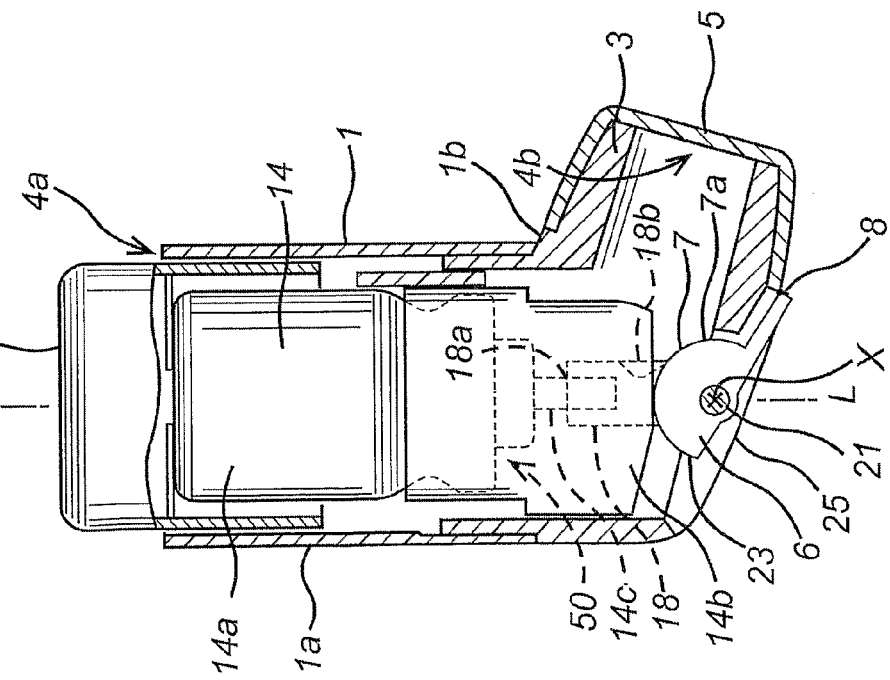

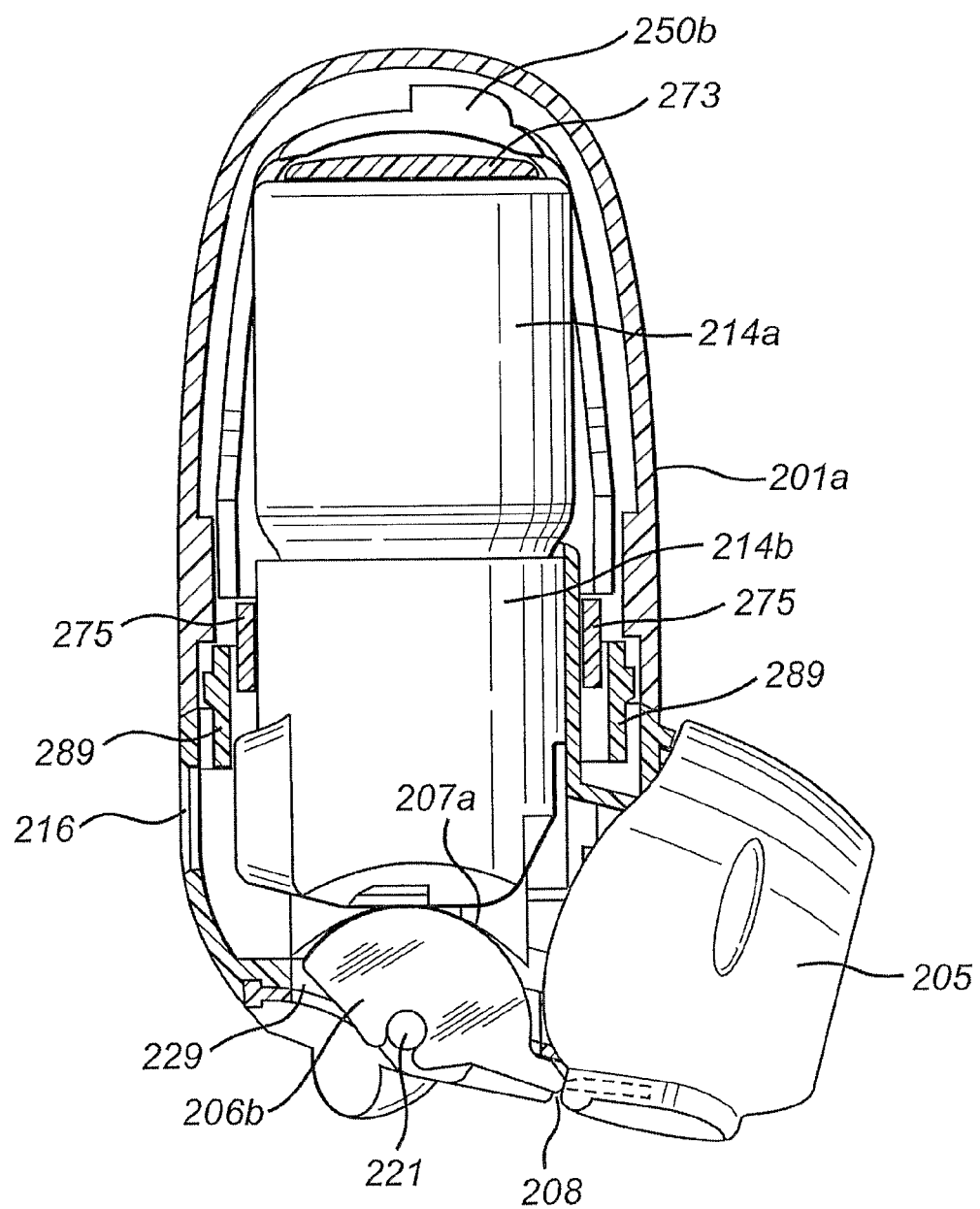

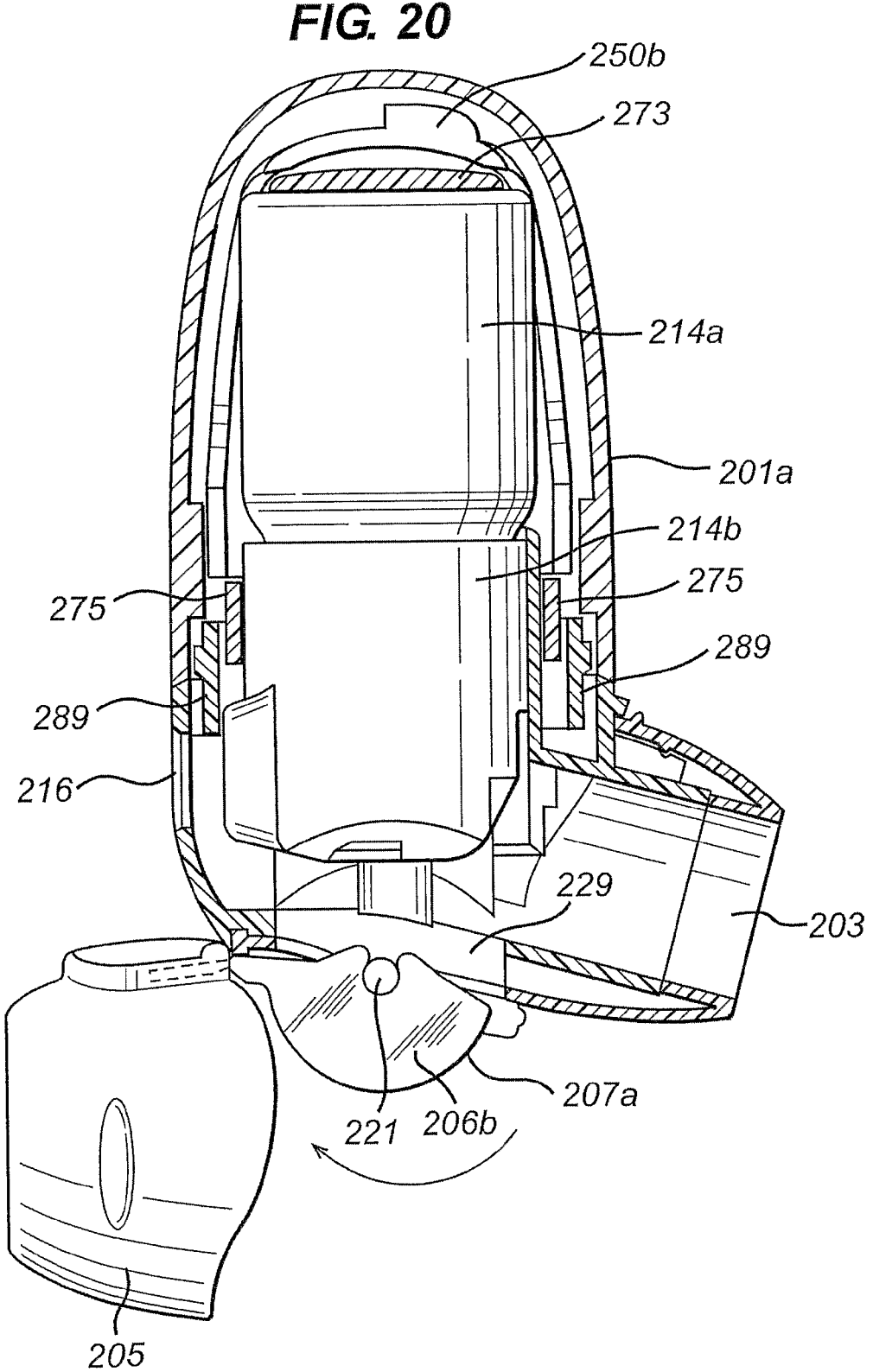

INHALER

RELATED APPLICATION

This application is filed pursuant to 35 U.S.C. §371 as a United States National Phase Application of International Patent Application Serial No. PCT/GB2006/003307 filed 7 Sep. 2006, which The present application claims priority from UK Patent Application No. 0518355.3 filed on 8 Sep. 2005, the entire content of which is hereby incorporated herein by reference.

FIELD OF THE INVENTION

The present invention relates to an inhaler for use with a container unit containing a medicament formulation to be dispensed. An example of an inhaler to which the invention is particularly, but not exclusively, concerned is a pressurised metered dose inhaler (hereinafter referred to as a "pMDI").

BACKGROUND OF THE INVENTION pMDIs are well known in the art of inhalation devices. It is therefore not necessary to describe the construction and operation of a pMDI other than in bare essentials.

A pMDI comprises a canister unit and a housing. The housing is generally tubular, although this is not essential, and generally formed of a plastics material, for instance by moulding. The canister unit comprises an open-ended canister, typically made from a metal such as aluminium. The open end of the canister is sealingly capped by a metering valve assembly. The valve assembly includes a hollow dispensing member or valve stem which projects from the outlet or business end of the canister. The dispensing member is mounted for sliding movement relative to the canister between an extended position, to which the dispensing member is biased by a biasing mechanism in the valve assembly, and a depressed position.

In use, the sealed canister contains a pressurised medicinal aerosol formulation. The formulation comprises the medicament and a fluid propellant, and optionally one or more excipients and/or adjuvants. The medicament is typically in solution or suspension in the formulation. The propellant is typically a CFC-free propellant, suitably a liquid propellant, and may for example be HFA-134a or HFA-227.

Movement of the dispensing member from the extended position to the depressed position results in a metered dose of the aerosol formulation being dispensed from the canister through the dispensing member. Typically, the metering valve assembly is provided with a metering chamber of defined volume. In the extended position of the dispensing member, the content of the canister is placed in fluid communication with the metering chamber through the dispensing member so that the metering chamber is filled with the aerosol formulation. When the dispensing member is depressed, the metering chamber is isolated from the canister inner volume and placed in fluid communication with the external environment through the dispensing member. Thus, the defined volume of the aerosol formulation in the metering chamber is discharged to the external environment via the dispensing member.

Such metering valve assemblies are well known in the art and can be obtained from inter alia Bespak Plc (King's Lynn, Norfolk, United Kingdom) and Valois S.A.S. (Le Neubourg, France).

The housing comprises an internal passageway having an open end. The canister unit is slidable into the internal passageway through the open end with the canister unit being inserted valve assembly first into the internal passageway. A stem block, which receives the dispensing member of the canister when the canister unit is received in the housing in a "rest position", has a passageway with an inlet end for receiving the dispensing member and an outlet end, which faces a dispensing outlet of the housing, typically a mouthpiece or a nasal nozzle. The stem block holds the dispensing member stationary whereby depression of the canister unit from its rest position further into the housing to an "actuated position" causes the dispensing member to be displaced from the extended position to the depressed position relative to the canister. A metered dose of the aerosol formulation will thereby be dispensed out of the dispensing outlet of the housing via the internal passageway of the stem block.

In use, a patient in need of a metered dose of the medicinal aerosol formulation concurrently inhales on the dispensing outlet and depresses the canister unit from the rest position to the actuated position. The inspiratory airflow produced by the patient entrains the metered dose of the medicinal aerosol formulation into the patient's respiratory tract. This is known in the art as a "breath-coordinated" inhaler because the patient has to coordinate their inhalation with actuation of the inhaler.

Inhalers are commonly provided with a dust cap that covers the dispensing outlet when the inhaler is not in use. The dust cap, when applied, prevents foreign material from entering the housing. This prevents the user from inhaling dust or lint, for example, that might otherwise accumulate in the housing. This is of particular importance where the user suffers from asthma or other respiratory conditions, in which the inhalation of foreign material may cause severe irritation.

Developments to pMDIs have included the provision of actuation indicators or dose counters therefor. Such a dose counter is described in WO-A-9856444, corresponding to U.S. Pat. No. 6,431,168, and WO-A-2004/001664, corresponding to US-A-2006/0096594 of Glaxo Group Limited, all of which are incorporated herein by reference. The pMDI canister unit may comprise the dose counter, which is fixably secured on the valve assembly end of the canister and includes a display which denotes the number of metered doses of the medicament formulation dispensed from, or remaining in, the canister. The display of the dose counter is visible to the patient through a window provided in the housing. The display may be presented by a plurality of indicator wheels rotatably mounted on a common axle, each wheel having numerals from '0' to '9' displayed in series around the circumference.

pMDI devices, however, are susceptible to unintentional actuation, particularly whilst in transit, for example shipment between the manufacturer and distributor. During such transit, such devices and their packaging are often subjected to impacts and sudden movements. Such forces can actuate the pMDI, causing doses of the formulation to be dispensed. When the pMDI includes a dose counter, rough handling in transit can cause the value displayed to the user by the counter to increase or decrease so that it is not consistent with the number of doses that have been dispensed by, or remain in, the pMDI. It is wasteful to dispense unwanted doses of the medicament, and potentially very dangerous for a dose counter to indicate to the user that more doses remain in the canister than are actually present.

Methods of dealing with this problem of unintentional actuation of pMDI devices have previously been described. WO-A-0587299 in the name of Glaxo Group Limited describes a pMDI with a restricting member to prevent unintentional actuation of the inhaler. The restricting member described therein is provided on the inhaler closure and enters the housing through the dispensing outlet when the closure is positioned to close the dispensing outlet. UK Patent Application No. 0505543 and counterpart PCT Patent Application PCT/GB2006/000978, also in the name of Glaxo Group Limited, describe an actuator for a PMDI which comprises a priming mechanism having a support member which includes a stem block. The support member is movable relative to the inhaler housing between a first, inoperative position in which actuation of the inhaler is not possible and a second position in which actuation is possible. U.S. Pat. No. 5,447,150 in the name of Norton Healthcare Limited describes a breath-operated pMDI with a pivotally attached dust cap capable of covering the inhaler mouthpiece. The inhaler may not be actuated when the dust cap is in the closed position.

A multiple-dose DPI with means of preventing unintentional actuation is marketed under the trademark Easyhaler®, the basic inhaler construction being illustrated in WO-A-01/87391 (Orion Corporation). The Easyhaler® inhaler dispenses a powdered medicament when a dosing member is moved, relative to the body of the inhaler, towards a metering drum. This movement causes the drum to rotate, dispensing a single metered dose of the powdered medicament from a powder reservoir at an inhaler mouthpiece for entrainment in the inhalation airflow of a user inhaling thereat, and driving a dose counting mechanism. The inhaler also comprises a small hole through the body of the inhaler, situated above the mouthpiece. A cap is provided, to cover the mouthpiece when not in use, comprising a prong that protrudes through the hole and into the body of the inhaler when the cap is engaged by the mouthpiece. The presence of the prong inside the body of the inhaler restricts the motion of the dosing member in the direction of the drum, preventing the user from dispensing powder by pressing down on the dosing member while the cap is engaged.

An aim of the invention is to provide an inhaler with a novel means of preventing unintentional actuation thereof.

SUMMARY OF THE INVENTION

One aspect of the present invention provides an inhaler for use with a container unit containing a medicament formulation to be dispensed. The inhaler comprises: a housing for the container unit and in which the container unit is relatively movable thereto to cause dispensing of a dose of the medicament formulation from the container unit for inhalation by a user through a dispensing outlet of the inhaler; a closure movable between a closed position, in which the closure closes the dispensing outlet, and an open position, in which the dispensing outlet is open; and a revolvable element comprising a restricting member, the revolvable element in use being revolvable around an axis between a first position, which places the restricting member in a non-restricting position which does not restrict relative movement between the container unit and the housing for dispensing of the dose of the medicament formulation, and a second position, which places the restricting member in a restricting position which does restrict relative movement between the container unit and the housing such that dispensing of the dose of the medicament formulation is prevented; wherein the closure is associated with the revolvable element such that movement of the closure from the closed position to the open position causes the revolvable element to move the restricting member from the restricting position to the non-restricting position and vice-versa.

Other aspects and optional features of the invention are set forth in the appended claims and in the non-limiting exemplary embodiments of the invention which will now be described with reference to the accompanying Figures of drawings.

BRIEF DESCRIPTION OF THE DRAWINGS

FIG. 2 is a part-sectional side view of the first pMDI showing a container unit mounted in a housing whose dispensing outlet is closed by a closure to which a generally 'P'-shaped revolvable restricting member is associated by a hinge such that the restricting member restricts movement of the canister unit in the housing to prevent dispensing therefrom.

FIGS. 3 to 6 correspond to FIG. 2, but sequentially show how movement of the closure from the closed position to an open position causes the associated 'P'-shaped revolvable restricting member to be revolved into a position which no longer restricts relative movement between the housing and the container unit whereby dispensing from the container unit out of the dispensing outlet can take place.

FIG. 19 is a part-sectional side view showing the third embodiment with the closure in the closed position and the revolvable element in the restricting position such that dispensing of the dose of the medicament formulation is prevented.

FIG. 20 is a part-sectional side view showing the third embodiment with the closure in the open position and the revolvable element in the non-restricting position such that dispensing of the dose of the medicament formulation is not prevented.

DETAILED DESCRIPTION OF THE EXEMPLARY EMBODIMENTS

Figure 1:
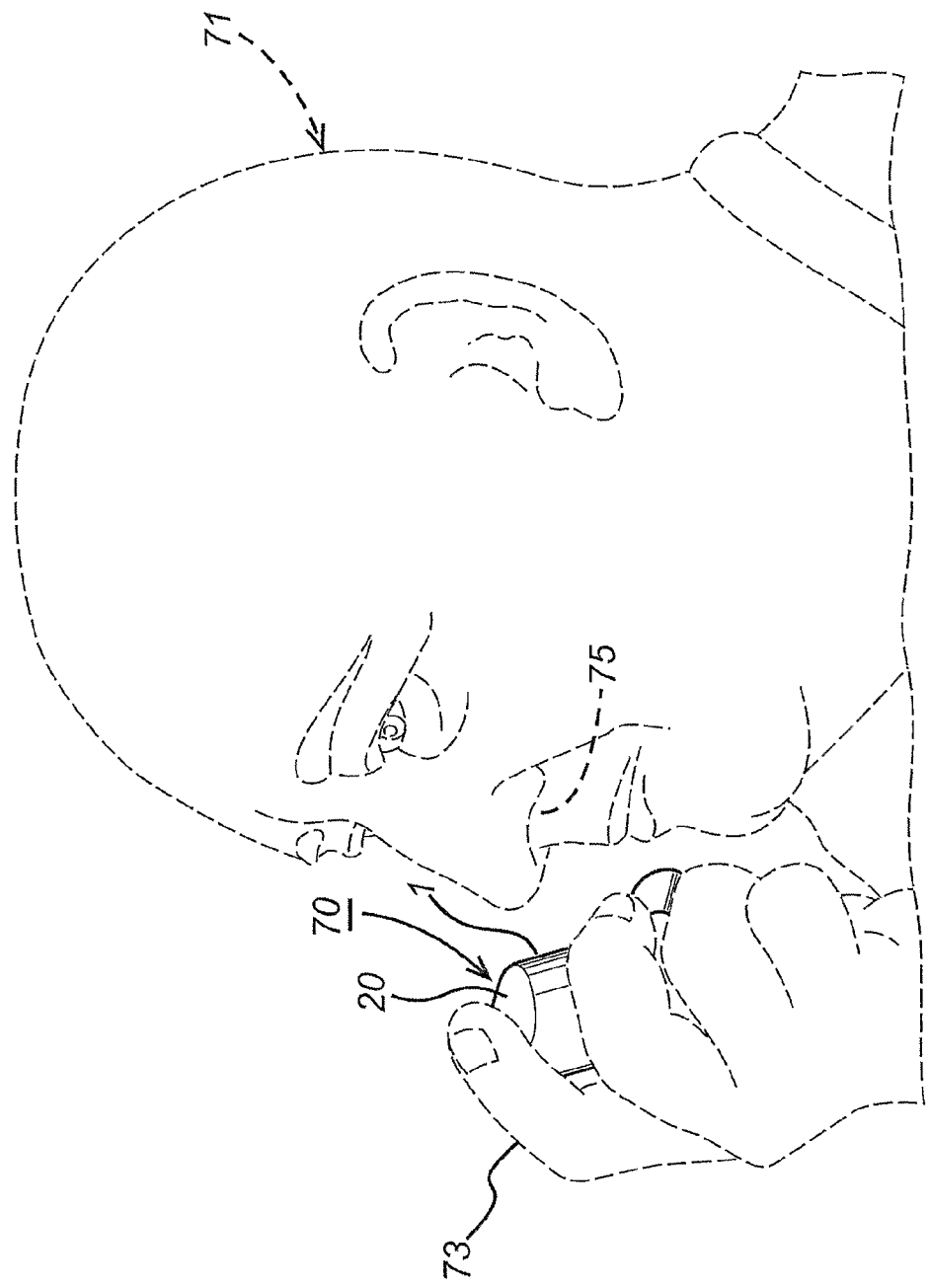
FIG. 1 shows a first pMDI according to the invention in use.

In the following detailed description of the different exemplary embodiments, like references numbers denote like features to avoid unnecessary duplication of the description of such features.

FIGS. 1 to 6 are views showing a hand-held, hand-operable, breath-coordinated pMDI 70 according to a first embodiment of the present invention for use by a patient 71. The pMDI 70 comprises a container unit 14 and a housing 1 in which the container unit 14 is slidable along its longitudinal axis L-L. The housing 1 is generally tubular and of L-shape having an axial section 1a and a transverse section 1b configured as a mouthpiece 3. In an alternative embodiment, the transverse section 1b is configured as a nasal nozzle for insertion into the patient's nostril 75.

The housing 1 may be moulded from a plastics material, for example by injection moulding. Conveniently, the housing is of polypropylene. In the use orientation of the pMDI 70 shown in FIGS. 2 to 6, the housing 1 has an upper end 4a in the axial section 1a, through which the container unit 14 is insertable into the housing 1, and a lower open end 4b in the mouthpiece 3.

Figure 6:
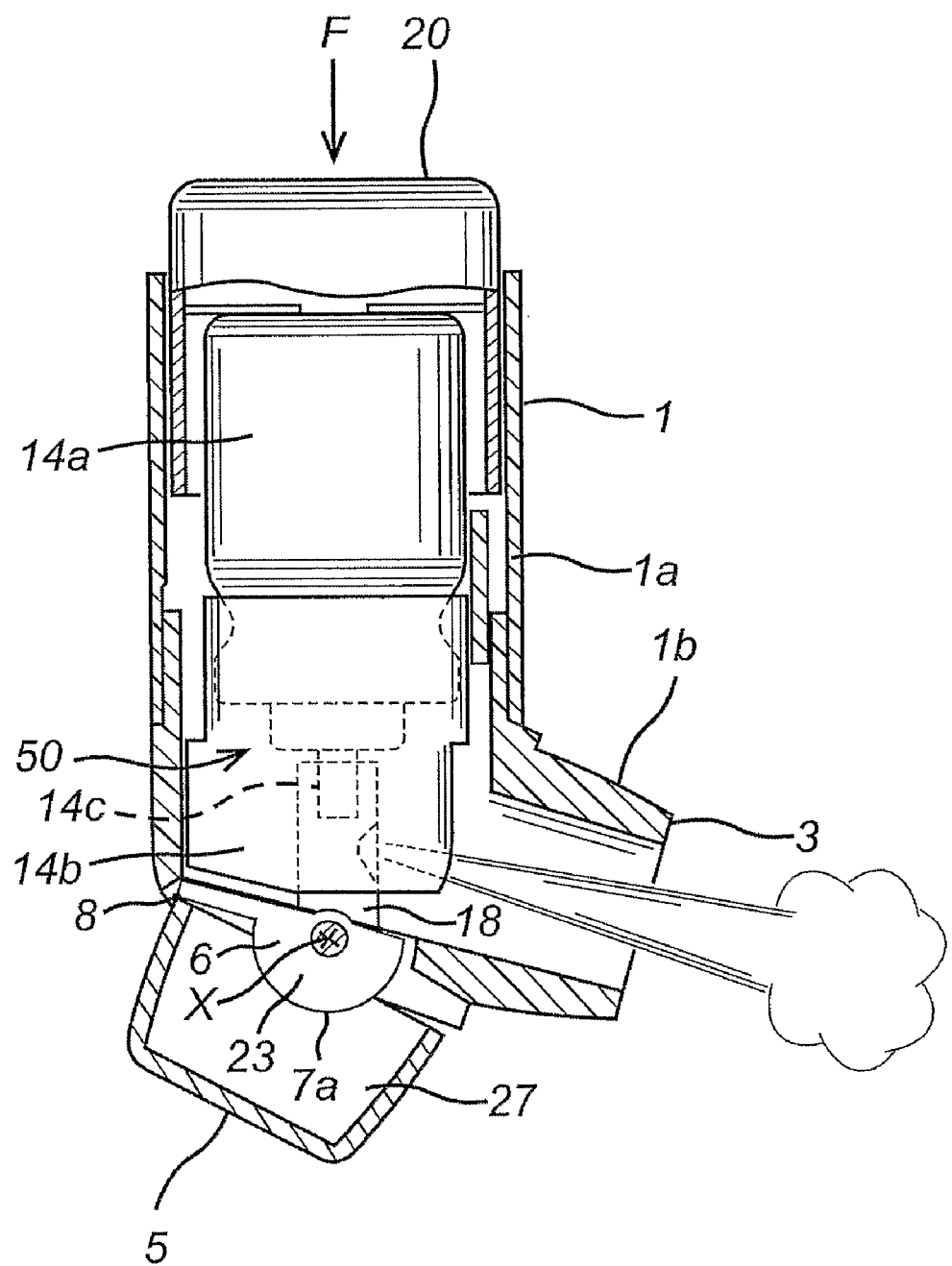
Figure 7:
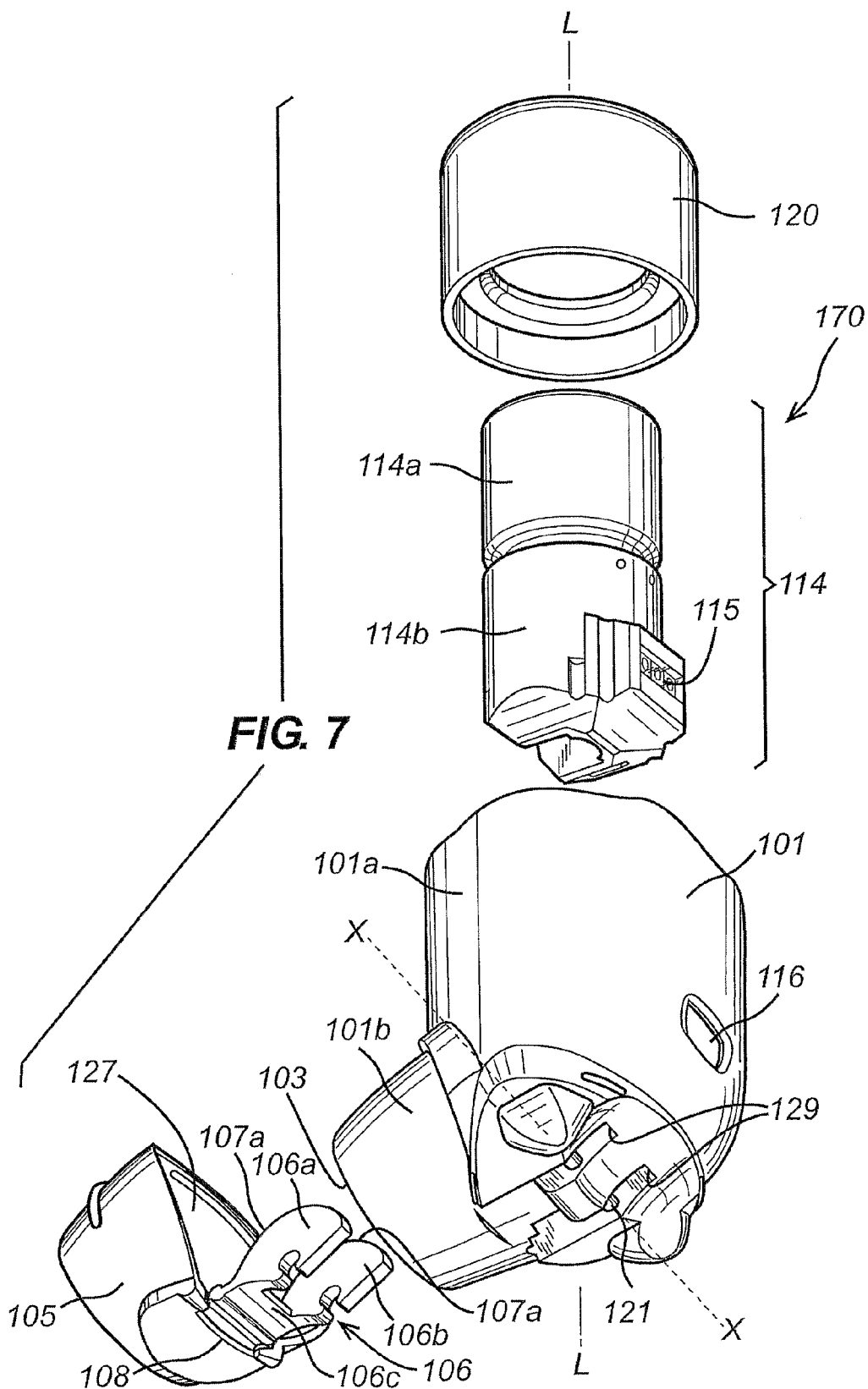
FIG. 7 is an exploded perspective view from below of a second pMDI according to the present invention which comprises a housing with a mouthpiece, a container unit for mounting in the housing, a closure for closing the mouthpiece, a cap for actuating the pMDI and a pair of generally 'P'-shaped revolvable restricting members associated with the closure.
Figure 8:
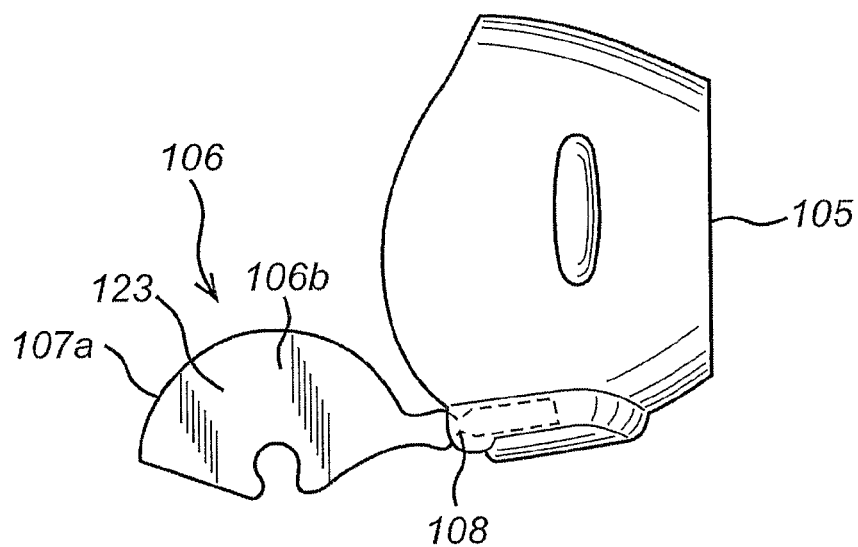
FIG. 8 is a side view of the closure of the second pMDI and the associated revolvable restricting member.
Figure 9:
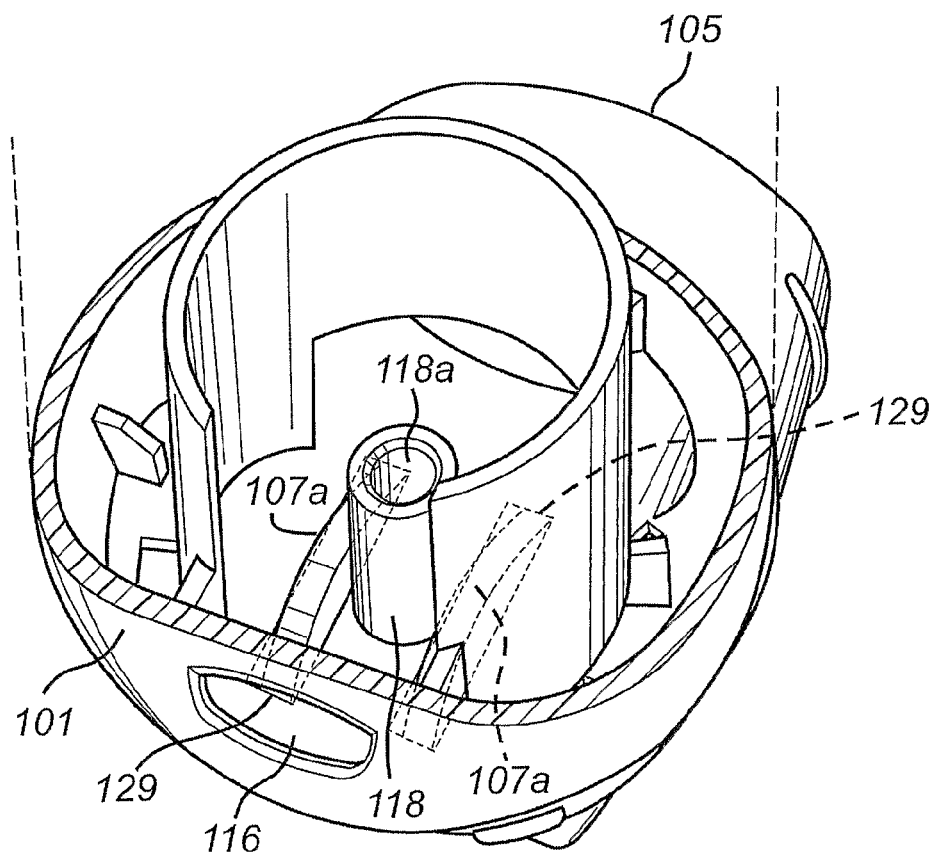
FIG. 9 is a fragmentary perspective view from above of the closure in a closed position on the mouthpiece and the restricting surfaces of the associated revolvable restricting member in a restricting position on either side of a stem block.
Figure 10:
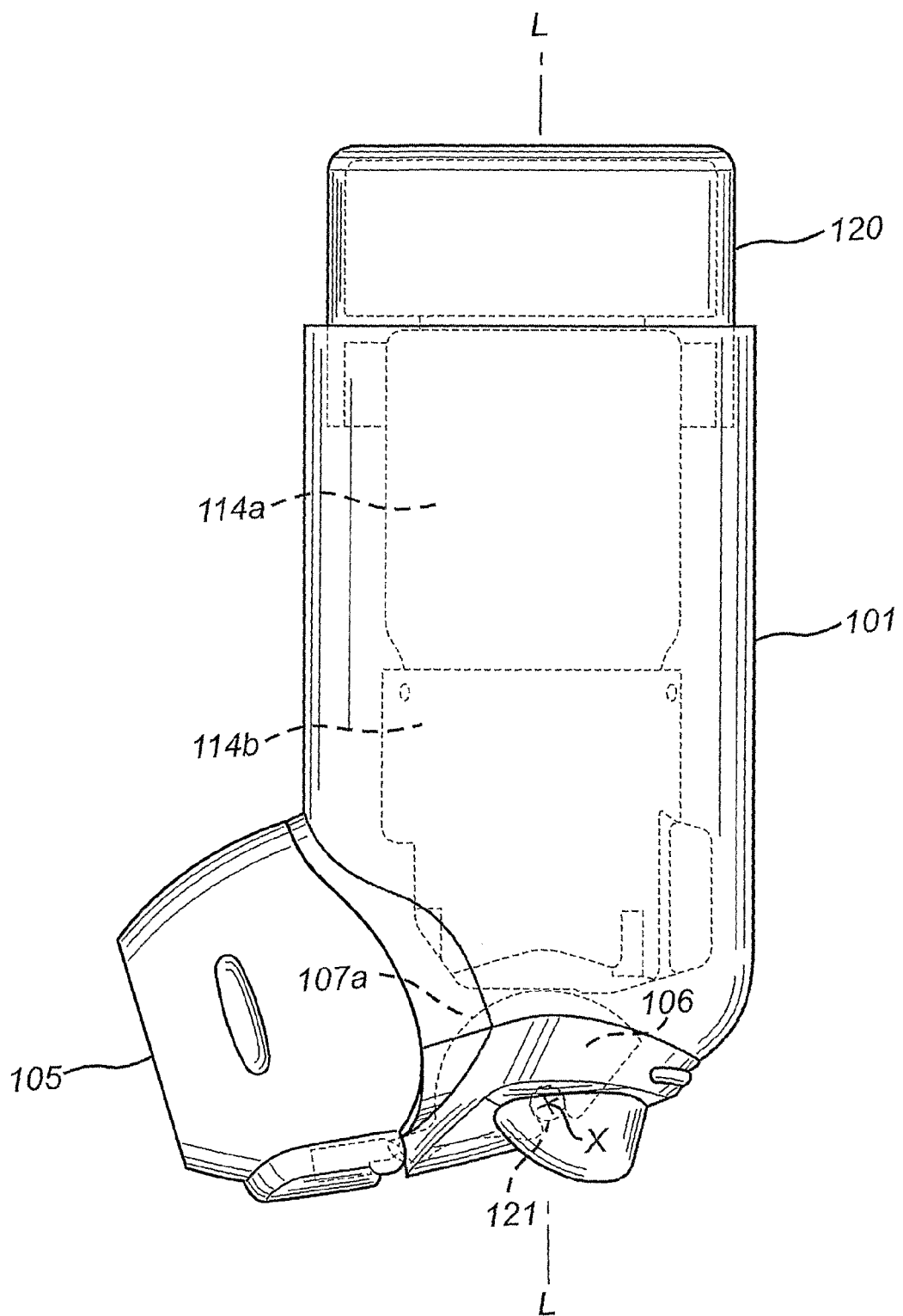
FIG. 10 is a side view of the second pMDI with the closure in its closed position and the restricting surfaces of the associated revolvable restricting member in a restricting position on either side of the stem block.
Figure 11:
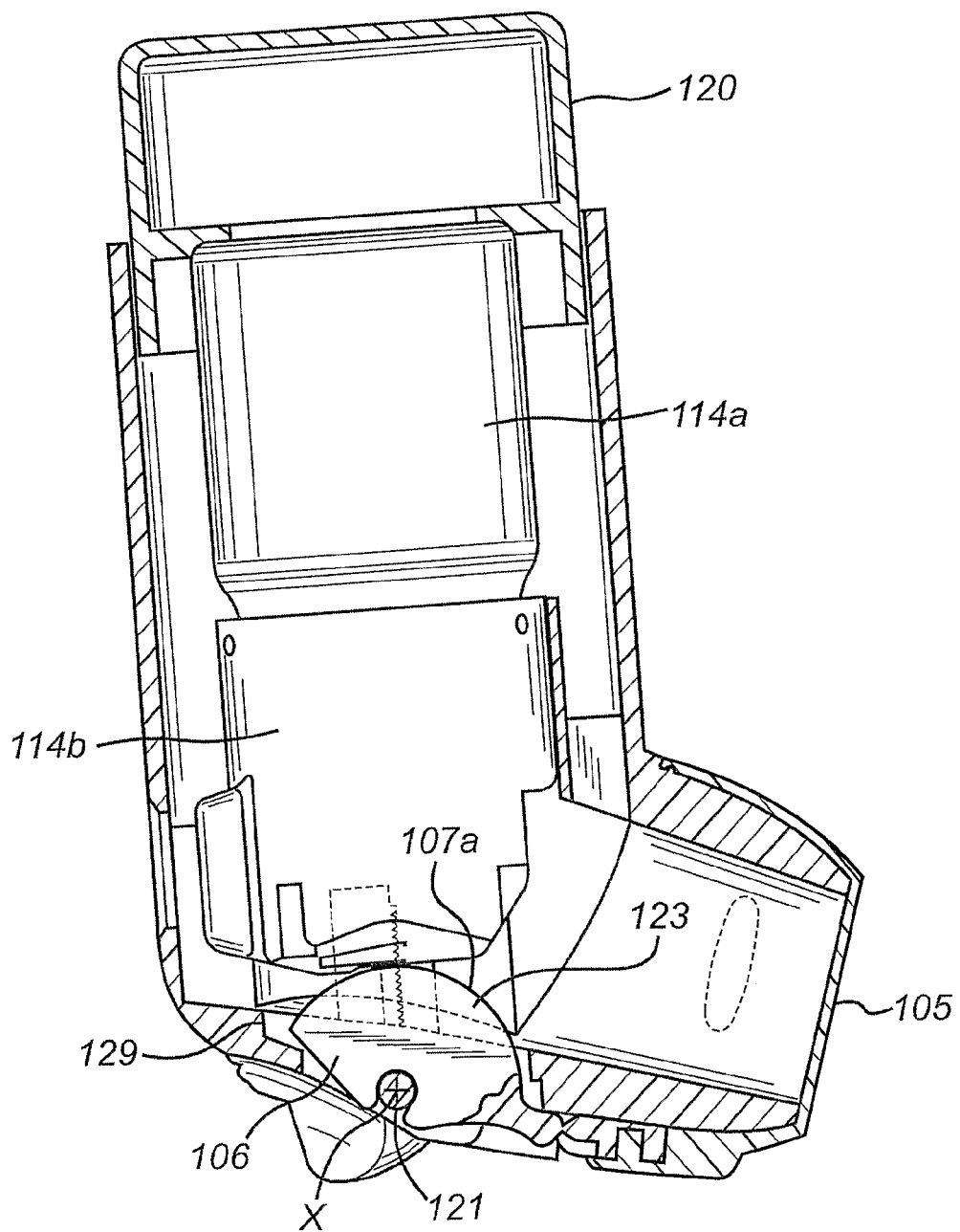
FIG. 11 is a partial cross-sectional view corresponding to FIG. 10.
Figure 12:
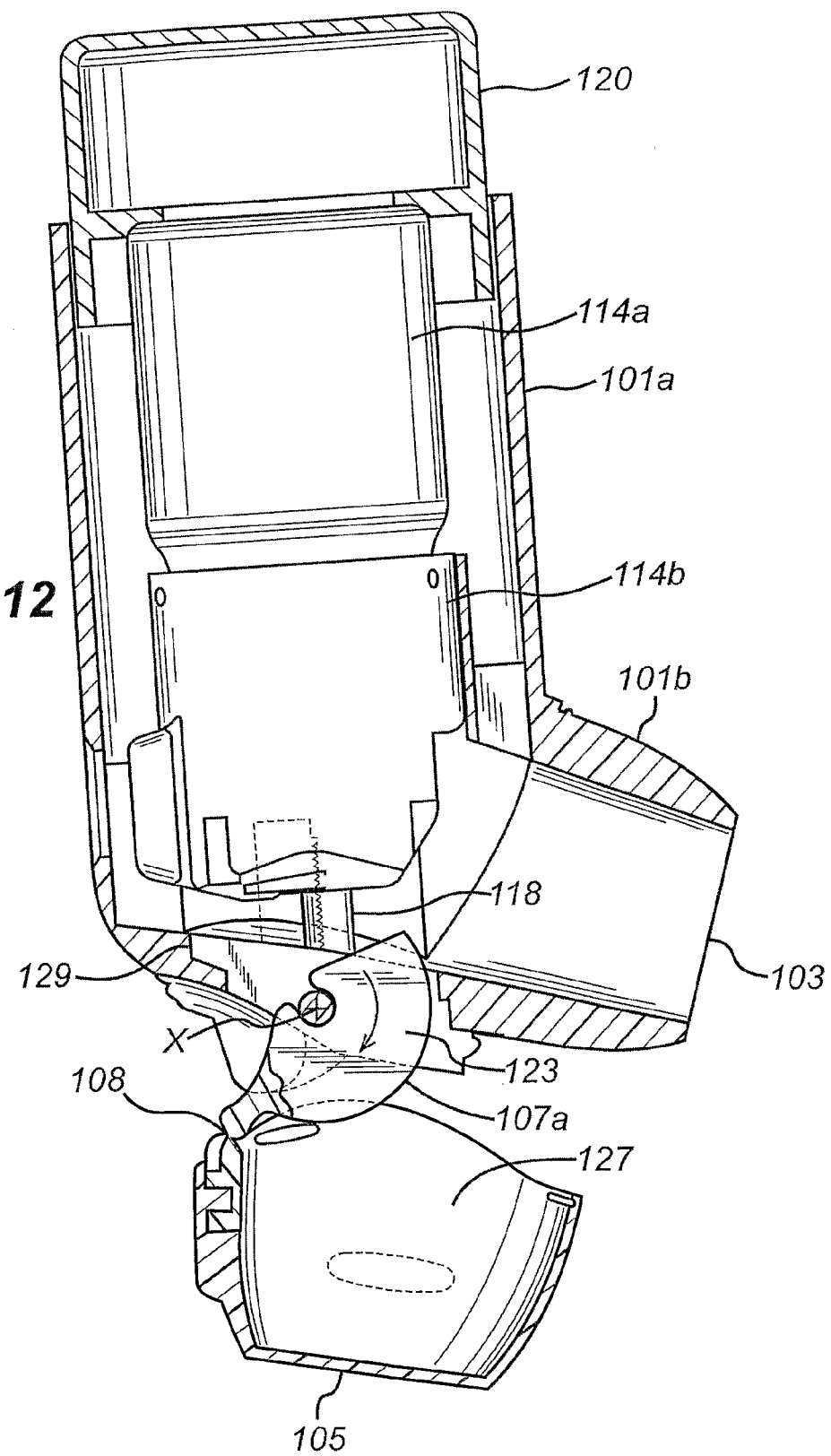
FIG. 12 is a partial cross-sectional view showing the second pMDI with the closure in an intermediate position between the closed position and an open position.

The pMDI 70 further comprises a cap 20 which covers the upper end of the container unit 14 and is also reversibly slidable into the housing 1. Downward application of pressure by the user 71 causes the cap 20 to push the container unit 14 into the housing 1, provided that a closure 5 is in the open position, as depicted in FIG. 6.

The container unit 14 comprises a pressurised aerosol canister 14a having a metering valve 50 at its leading or business end and a dose counter module 14b mounted on the leading (valve) end of the canister 14a. Metering valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. Spraymiser™). An exemplary metering valve is disclosed in U.S. Pat. Nos. 6,170,717, 6,315,173 and 6,318,603. The metering chamber (not shown) of the metering valve 50 may be coated with a fluorinated polymer coating, for instance by cold plasma polymerisation, as detailed in US-A-2003/0101993. The canister 14a contains a pressurised medicinal aerosol formulation, as known in the art and mentioned briefly hereinabove. The canister 14a may be made of aluminium and may have its inner surfaces coated with a fluorocarbon polymer, optionally blended with a non-fluorocarbon polymer, for example a blend of polytetrafluoroethylene (PTFE) and polyethersulphone (PES). In this regard, reference may be had to U.S. Pat. Nos. 6,143,277, 6,511,653, 6,253,762, 6,532,955 and 6,546,928. The dose counter module 14b is as described in PCT Patent Application No. WO-A-2004/001664 and its US equivalent US-A-2006/0096594. The dose counter module 14b is fixably secured on the valve assembly end of the canister 14a and includes a display which denotes the number of metered doses of the medicament formulation remaining in the canister 14a. The display of the dose counter module 14b is visible to the patient through a window provided in the housing 1. The display of the dose counter module 14b and the housing window are not shown in the first embodiment. However, they are illustrated in FIGS. 7 to 13 showing a second embodiment, the display being labelled 115 and the window labelled 116.

A hollow stem block 18 protrudes vertically from an internal basal surface of the housing 1 along axis L-L. The stem block 18 receives a valve stem 14c of the metering valve assembly 50 when the container unit 14 is received in the housing 1 in a "rest position". The stem block 18 has an internal passageway with an inlet end 18a for receiving the valve stem 14c and an outlet end 18b, which faces the mouthpiece 3. The stem block 18 holds the valve stem 14c stationary whereby depression of the cap 20 and thereby the container unit 14 from its rest position further into the housing to an "actuated position" causes the valve stem 14c to be displaced from an extended position to a depressed position relative to the canister 14a. This displacement causes a metered dose of the aerosol formulation to be dispensed from the canister 14a, through the outlet end 18b of the stem block 18 and out of the mouthpiece 3, as indicated in FIG. 6.

In use, a patient 71 in need of a metered dose of the medicinal aerosol formulation places his or her lips on the mouthpiece 3 of the housing 1 and then concurrently inhales and, with their finger(s) 73, depresses the container unit 14 into the housing 1 by applying downward pressure to the cap 20 (arrow F, FIG. 6) to cause the metering valve 50 to release a metered dose of the medicinal formulation from the container unit 14 for entrainment in the inspiratory airflow produced by the patient for deposition in their lungs. In other words, the patient 71 has to coordinate their inhalation with the actuation of the pMDI 70, hence the term "breath-coordinated inhaler". The depression of the container unit 14 into the housing 1 also results in the dose counter module 14b recording the release of the dose and showing the number of metered doses left in the canister 14a, as described in WO-A-2004/001664 supra.

In the embodiment shown in FIGS. 1 to 6, the pMDI 70 comprises a revolvable element 6 which is revolvably mounted in a slot 29 in a base 25 of the housing 1 and further which is associated with a closure 5 for closing the mouthpiece 3 when the pMDI 70 is not in use. The closure 5 may be moulded, for example by injection moulding, from a plastics material, for example polypropylene. Conveniently, the closure 5 and the revolvable element 6 may form a single component part of the pMDI 70, e.g. a single moulded part. The revolvable element 6 revolves around a fixed axis X which passes through the body of the revolvable element 6 and through the housing 1. Moreover, the fixed axis X is perpendicular to the longitudinal axis L-L. In this embodiment, the fixed axis X takes the form of the axis of an axle 21 around, or on, which the revolvable element 6 revolves. As shown in FIGS. 2 to 6, the revolvable element 6 has a generally 'P'-shaped body and the fixed axis X passes through the generally semicircular part 23 of the 'P'-shaped body.

Figure 5:
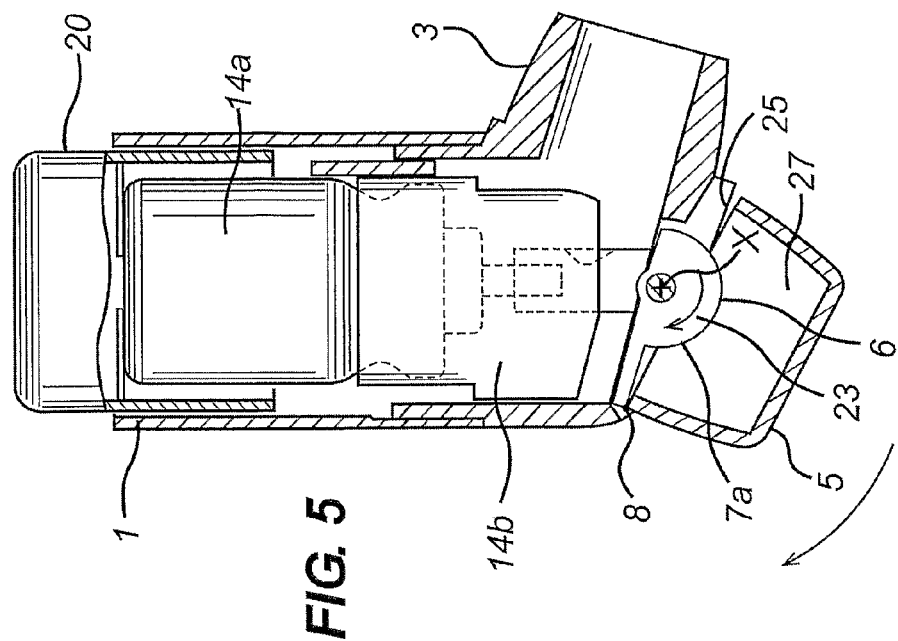
Figure 4:
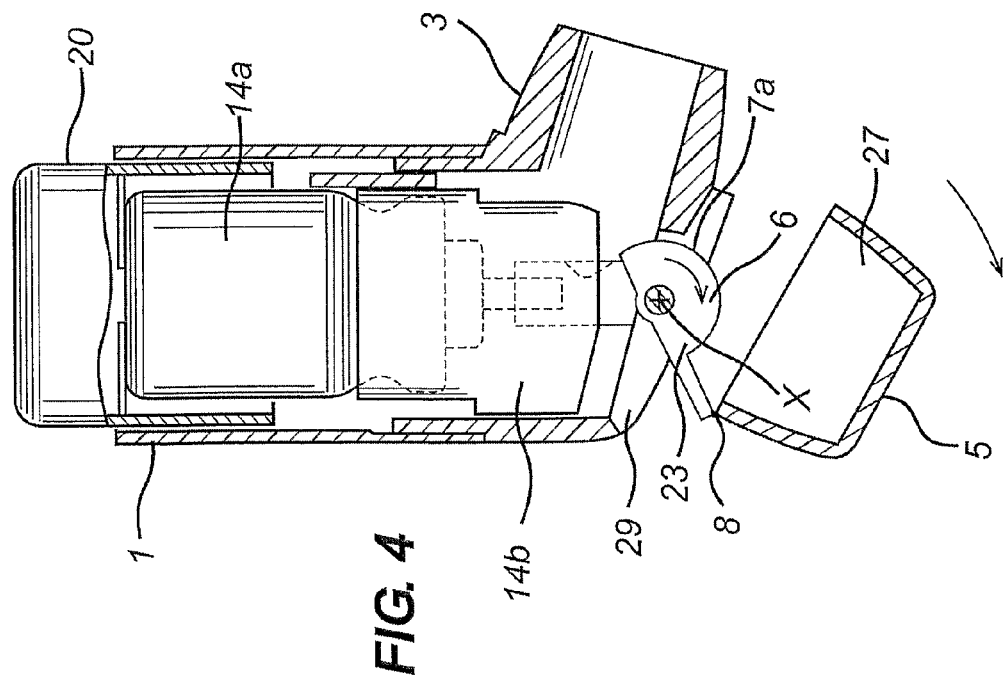

In the open position of the closure 5 shown in FIG. 5, the generally semicircular part 23 of the 'P'-shaped revolvable element 6 faces outwards away from the housing 1. Conversely, in the closed position of the closure 5 shown in FIG. 2, the generally semicircular part 23 of the 'P'-shaped revolvable element 6 faces and protrudes inwards into the housing 1.

The revolvable element 6 is associated with the closure 5 by means of a hinge 8 therebetween, in this embodiment a so-called "living hinge". The provision of a hinge allows the closure 5 to precisely or closely match the dimensions of the mouthpiece 3 whilst remaining operably connected to the revolvable element 6. The closure 5 can swing downwards on the hinge 8 so as to uncover the mouthpiece 3 when the closure is being moved to the open position. To uncover the mouthpiece 3, the user simply pulls the closure 5 downwards and away from the mouthpiece 3 with sufficient force to overcome a snap-fit connection therebetween (not shown).

The hinge 8 also allows the angle between the closure 5 and the revolvable element 6 to change relative to each other whilst the revolvable element 6 revolves around the fixed axis X. Therefore, when moving the closure 5 to the open position, once the closure 5 has cleared the mouthpiece 3, the closure 5 may be pushed back beneath the mouthpiece 3, thereby causing the revolvable element 6 to revolve around its axis X, and secured to the base 25 of the housing 1, e.g. by means of a snap-fit or interference fit connection (not shown). When secured in this position the closure 5 covers the slot 29 and the revolvable element 6, the generally semicircular part 23 of which faces outwardly away from the housing 1. More particularly, the generally semicircular part 23 protrudes into the inner volume 27 of the closure 5.

In addition, when the closure 5 is in the open position as shown in FIG. 5, covering the revolvable element 6 and secured to the base 25 of the housing 1, it may form a seal between the closure 5 and the housing 1 and may, therefore, reduce airflow out of the slot 29 in the housing 1, in which the revolvable element 6 is revolvably mounted, during inhalation of a dose of the medicament formulation. By reducing the airflow through slot 29 the normal top to bottom airflow profile of the inhaler device during inhalation is less disrupted than would otherwise be the case.

In order to move the closure 5 from the open position back to the closed position the above process is simply reversed.

As will be gathered from the foregoing, when the closure 5 is moved from the open position to the closed position, the association of the closure 5 with the revolvable element 6 through the hinge 8 causes the revolvable element 6 to revolve around the fixed axis X. The revolvable element 6 defines a restricting member 7 which restricts movement of the container unit 14 in the housing 1 when the closure 5 is in the closed position whereby inadvertent dispensing from the canister 14a and concomitant counting by the dose counter module 14b is prevented. In this regard, the arcuate surface of the generally semicircular part 23 of the 'P'-shape defines a restricting surface 7a of the restricting member 7. When the closure 5 is moved from the open position to the closed position, the revolvable element 6 revolves around the fixed axis X in a counter-clockwise direction, when viewed as shown in FIGS. 2 to 6 and the restricting surface 7a is caused to move from facing outwards, away from the housing 1, to facing inwards into the housing 1. When inwardly facing, the restricting surface 7a is in a position to restrict relative movement between the container unit 14 and the housing 1 through abutment of the container unit 14 with the restricting surface 7a, more particularly abutment of the dose counter module 14b with the restricting surface 7a, and thus prevent inadvertent dispensing of a dose of the medicament formulation and counting by the dose counter module 14b when the pMDI 70 is not in use. Such inadvertent dispensing/counting might occur, for example, during shipping of the pMDI 70 from the manufacturer to the distributor, or when the pMDI 70 is in a patient's pocket or handbag, or even as a result of a person fiddling/playing with the pMDI 70. Wastage of the medicinal formulation is therefore reduced.

The revolvable element 6 and cap 20 may be moulded from a plastics material, for example by injection moulding. Conveniently, these elements are of polypropylene.

As shown in FIGS. 1 to 6, the restricting surface 7a abuts against, or is located in close proximity to, the lead ending of the counter module 14b when the closure 5 is in the closed position.

When the closure 5 is moved from the closed position to the open position, the association of the closure 5 with the revolvable element 6 through the hinge 8 causes the revolvable element 6 to revolve around the fixed axis X in the direction opposite to that revolved when the closure 5 is moved from the open position to the closed position as described above. Therefore, as the closure 5 is moved form the closed position to the open position, the revolvable element 6 revolves around the fixed axis X and the restricting surface 7a is caused to move from facing inwards into the housing, to facing outwards, away from the housing 1. When outwardly facing, the restricting surface 7a, just like all the other surfaces of the revolvable element 6, is not in a position to restrict relative movement between the container unit 14 and the housing 1 and thus the user is able to release a dose of the medicinal formulation by depressing the cap 20 when the closure 5 is in the open position. Moreover, the dose counter module 14b records the dose release.

A second hand-held, hand operable, breath-coordinated pMDI 170 of the invention is shown in FIGS. 7 to 13, only the features of which not exhibited by the first pMDI 70 being described in any detail hereinbelow.

The revolvable element 106 has two, spaced apart, parallel 'P'-shaped members, 106a and 106b. The revolvable element 106 has a bridging member 106c which connects the two 'P'-shaped members 106a and 106b. Each 'P'-shaped member 106a, 106b, presents a restricting surface 107a which functions in the same way as in the first embodiment of FIGS. 1 to 6. More particularly, the two restricting surfaces 107a are positioned on either side of the stem block 118 when the closure 105 is in the closed position (see FIG. 9) so as to restrict relative movement between the container unit 114 and the housing 101 and thus prevent inadvertent dispensing/counting of a dose of the medicament formulation. Such an arrangement allows the stem block 118 to be centrally located within the lateral section 101b of the housing 101 whilst providing stable restricting surfaces 107a to restrict relative movement between the container unit 114 and the housing 101 when the closure 105 is in the closed position.

A third hand-held, hand operable, breath-coordinated pMDI 270 of the invention is shown in FIGS. 14 to 20, only the features of which not exhibited by the first or second pMDIs 70; 170 being described in any detail hereinbelow.

Figure 17:
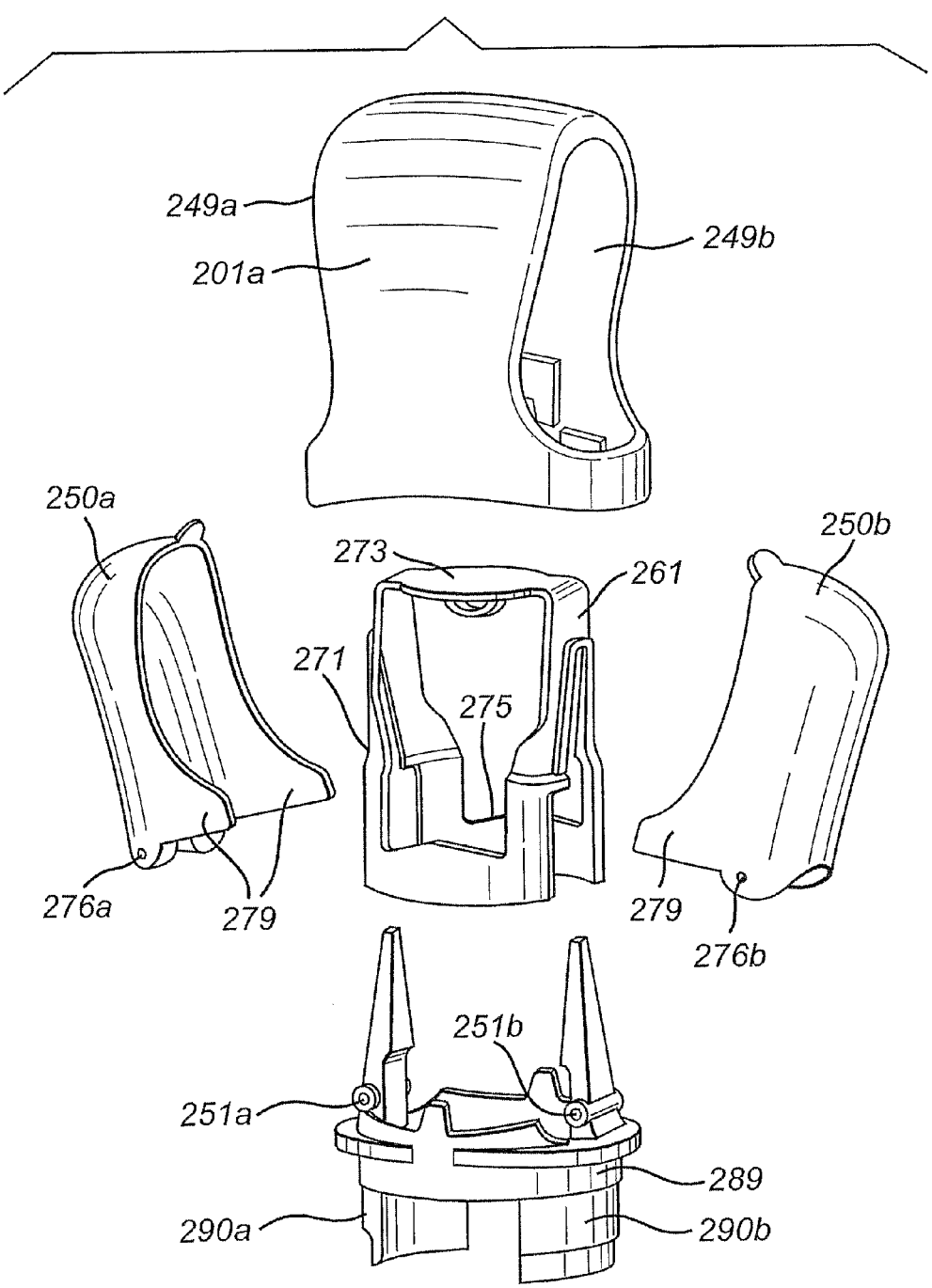
FIG. 17 is an exploded perspective view showing the component parts of the side actuation mechanism of the third embodiment.
Figure 18:
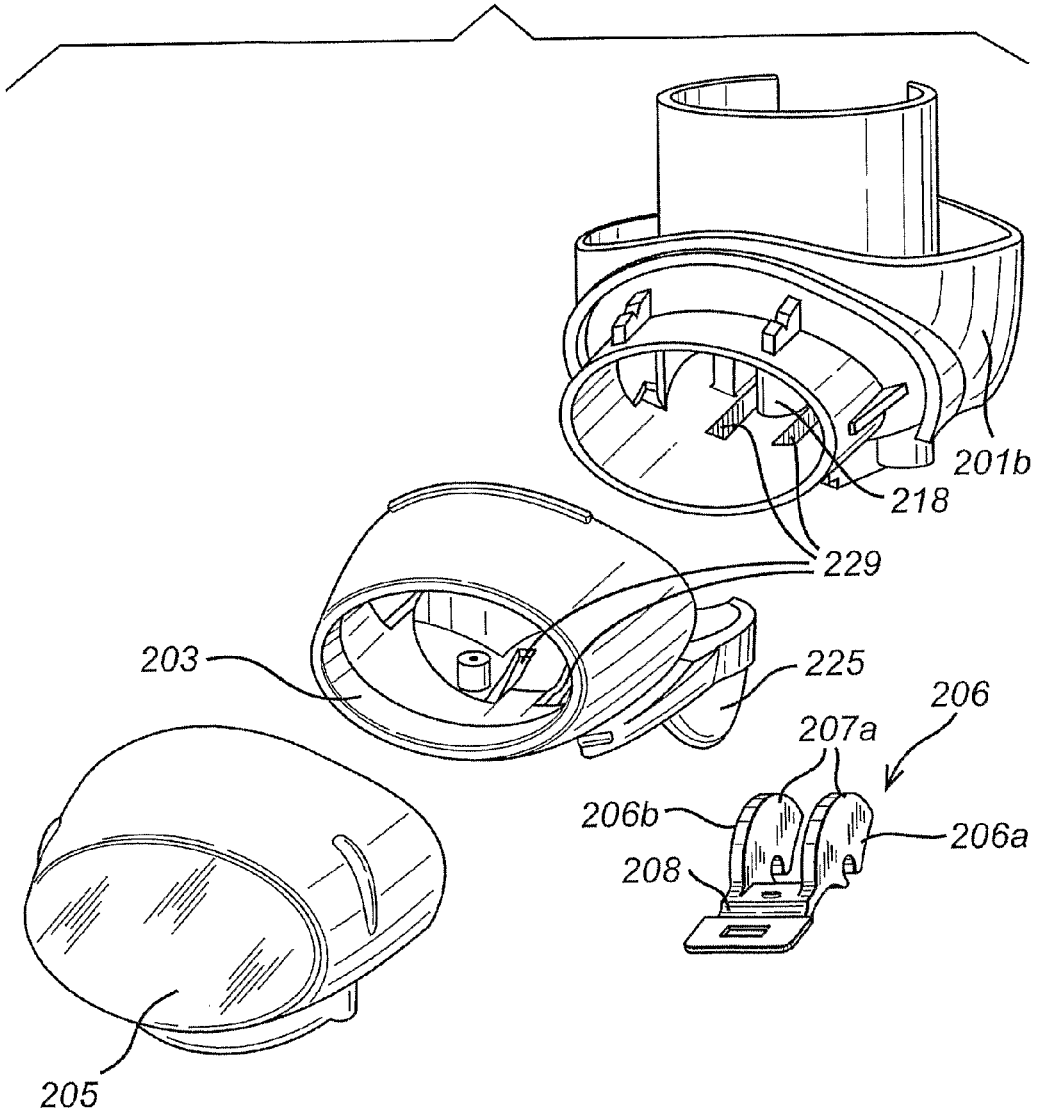
FIG. 18 is an exploded perspective view showing the lower housing, mouthpiece, closure and revolvable element of the third embodiment.

Dispensing of the dose of the medicament formulation is achieved by the user depressing side actuation levers 250a, b while holding the pMDI 270 with the closure 205 in the open position. As shown in FIGS. 17 and 18 the housing comprises two separate component parts, an upper housing 201a and a lower housing 201b assemblable by a bayonet fitting, infra. The lower housing 201b receives dose counter module 214b, which is attached to the leading edge of canister 214a, incorporates stem block 218 and axle 221 for securing the revolvable element 206. Mouthpiece 203 is not integrally formed with the lower housing 201b and instead forms a separate component part.

The upper housing part 201a comprises a hollow, shell-like upper body, of generally inverted T-shape, which presents lateral apertures 249a, b for receipt of the side actuation levers 250a, b respectively. The upper housing part 201a further comprises a chassis 289 which provides pivot elements 251a, b for engagement with pivot elements 276a, b of the levers 250a, b for pivotal movement thereof in the lateral apertures 249a, b between a rest position (FIGS. 14-16) and an inward, actuated position (not shown).

The chassis 289 includes a pair of arms 290a, b at its lower end which form the male part of a bayonet fitting which connects the upper and lower housing parts 201a, b to form the housing 201. The female part of the bayonet fitting is provided in the lower housing part 201b (not shown).

FIG. 17 shows a loading member 261 which translates the inward depression of the side actuation levers 250a, b into relative movement between the container unit 214 and the housing 201, and thereby dispensing of a dose of the medicament formulation. The loading member 261 is fitted over the container unit 214 and pivotal movement of the levers 250a, b between their rest and actuated positions provides for actuation of the canister 214a by engagement with the loading member 261.

The loading member 261 comprises a sleeve 271 which is a close fit with the outer peripheral wall of the canister 214a, an end section 273 at one, the upper, end of the sleeve 271, here which spans the sleeve 271, which engages the base of the canister 214a, and a loading section 275 which presents a flange, at the other, lower end of the sleeve 271, which is engaged by the actuating levers 250a, b to load the canister 214a.

FIG. 17 shows that the levers 250a, b are hollow, shell-like members, each presenting a pair of loading arms 279 which, in use, straddle the container unit 214 to act on the loading section 275 of the loading member 261 on opposing sides of the container unit 214.

Figure 15:
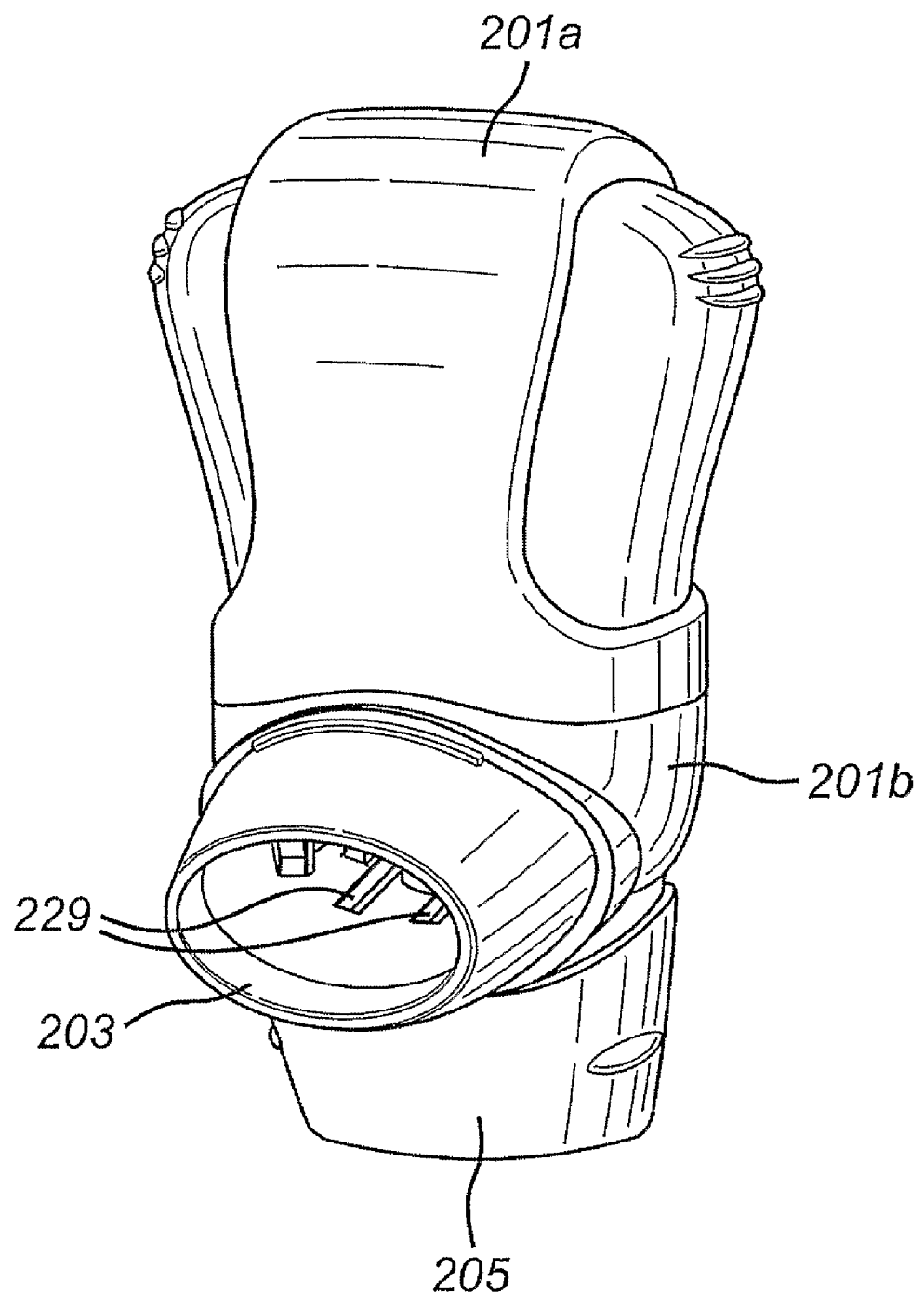
FIG. 15 is a perspective view showing the third embodiment with the closure in the open position and secured to the housing.
Figure 16:
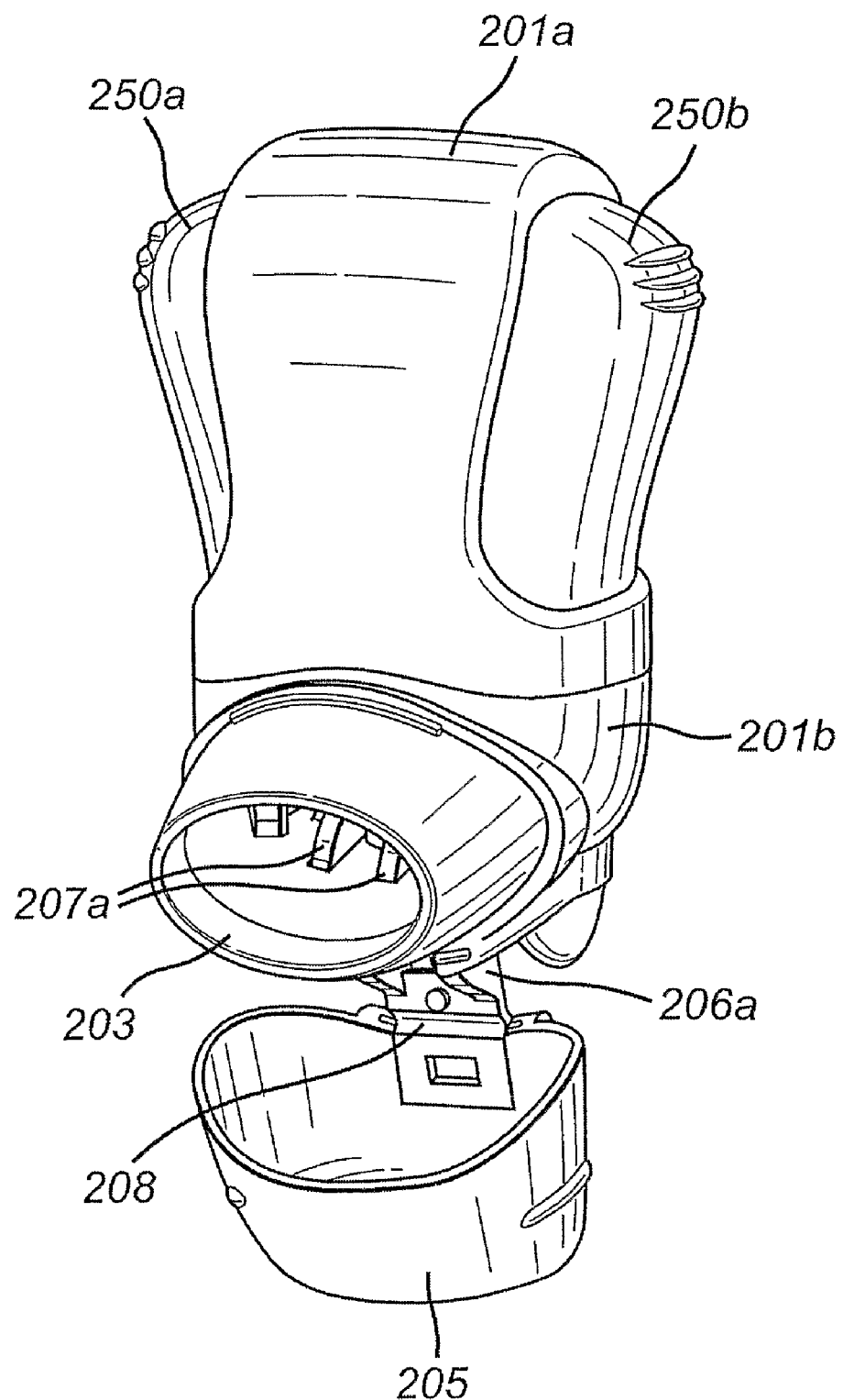
FIG. 16 is a perspective view showing the third embodiment with the closure in an intermediate position between the closed position and the open position, one of the restricting surfaces of the associated 'P'-shaped revolvable restricting member being visible through the mouthpiece.

To operate the pMDI 270, the user manually puts the pMDI 270 in the "mouthpiece open" configuration shown in FIG. 15, then takes the mouthpiece 203 in his/her lips, and, in co-ordination with an inhalation breath, actuates the inhaler by depressing the actuation levers 250a, b with one or more digits of the hand holding the pMDI 270. Depression of the levers 250a, b causes inward rotation thereof, such that the loading arms 279 of the levers 250a, b drive the loading section 275 of the loading member 261, and hence the loading member 261, downwardly, which downward movement of the loading member 261 drives the container unit 214 downwardly in relation to the valve stem (not shown) of the canister 214a which is held stationary by the stem block 218. More particularly, when the levers 250a, b are pivoted inwardly, the loading arms 279 operate on the loading section 275 to push the loading member 261 downwardly. This in turn causes the end section 273 of the loading member 261 to bear on the base of the canister 214a and to push container unit 214 downwardly in the housing relative to the stationary valve stem.

This downward movement of the container unit 214 in relation to the stationary valve stem actuates the canister 214a to deliver a metered spray of the medicament formulation from the valve stem into and through the mouthpiece 203.

The resulting downward movement of the container unit 214 in the housing 201 not only results in the metering valve being opened, for dispensement of a metered dose of medicament, but also the display of the dose counter module 214b being advanced, as detailed in WO-A-2004/001664 supra.

On releasing the levers 250a, b the pMDI 270 is reset by the return spring in the metering valve ready for subsequent actuation.

Following actuation, the pMDI 270 is removed from the user's mouth and the mouthpiece 203 closed by the closure 205, ready for subsequent actuation.

As will be seen from FIG. 18, in this embodiment of the invention the closure 205 and revolvable element 206 are formed as separate sub-components which are assemblable into a unitary component through any suitable connection, e.g. an interference fit or a snap-fit. The revolvable element 206 is integrally formed with the hinge 208. Conveniently, the closure 205 and revolvable element 206 are of a plastics material, more conveniently moulded plastics parts in which case the hinge 208 is a living hinge.

In a modification of the third embodiment, not shown, the levers 250a, b are integrally formed with the chassis 289, e.g. as a one-piece moulding. The levers 250a, b are linked to the chassis 289 through living hinges to provide the required pivotal movement of the levers 250a, b.

Figure 14:
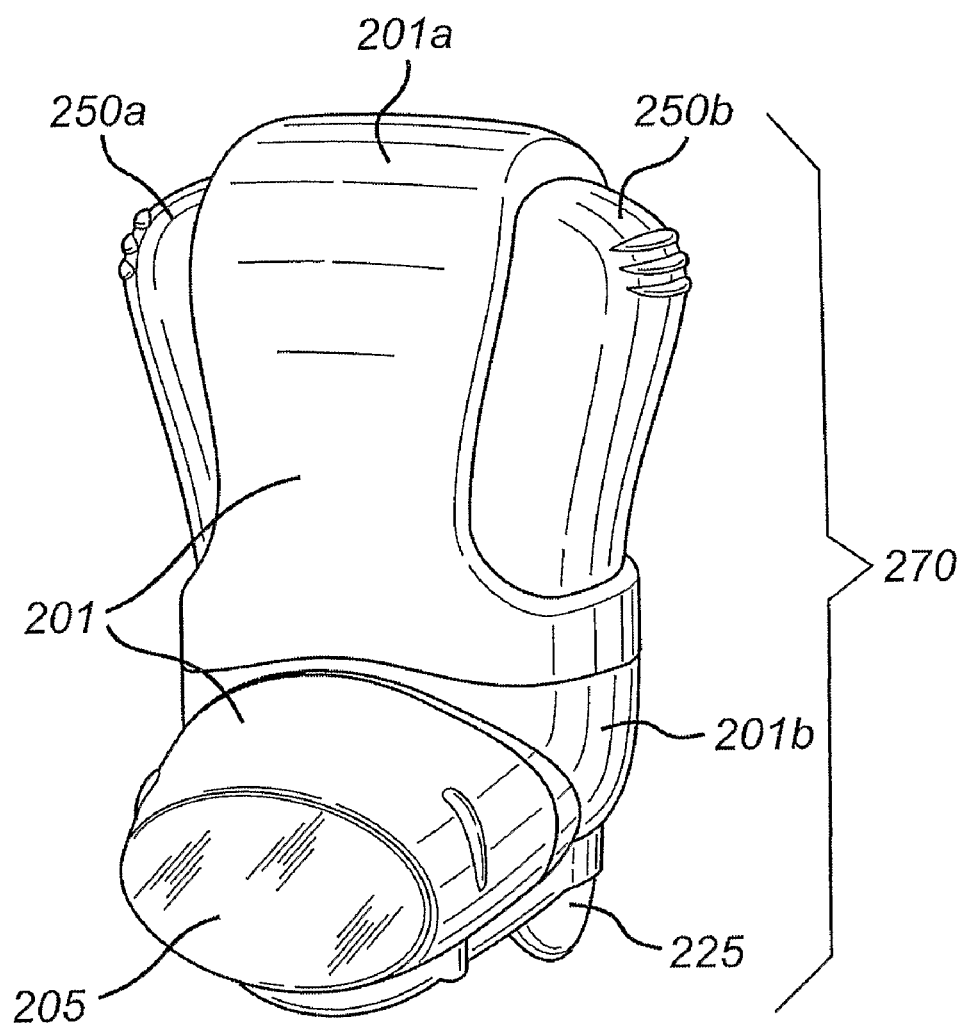
FIG. 14 is a perspective view of a third pMDI according to the present invention which comprises side actuation levers for dispensing a dose of the medicament formulation and where the closure is shown in the closed position.

Accidental dispensing of a dose of the medicament formulation is prevented when the closure 205 is in the closed position as shown in FIGS. 14 and 19 because the two restricting surfaces 207a of the two generally 'P'-shaped members 206a and 206b restrict relative movement between the container unit 214 and the housing 201 by abutting against the dose counter module 214b mounted at the leading end of the container unit 214. When the closure is in the open position, as shown in FIGS. 15 and 20, and the side actuation levers 250a, b are depressed by the user, the two restricting surfaces 207a of the two generally 'P'-shaped members 206a and 206b do not restrict relative movement between the container unit 214 and the housing 201, and thereby do not prevent dispensing of a dose of the medicament formulation.

Figure 13:
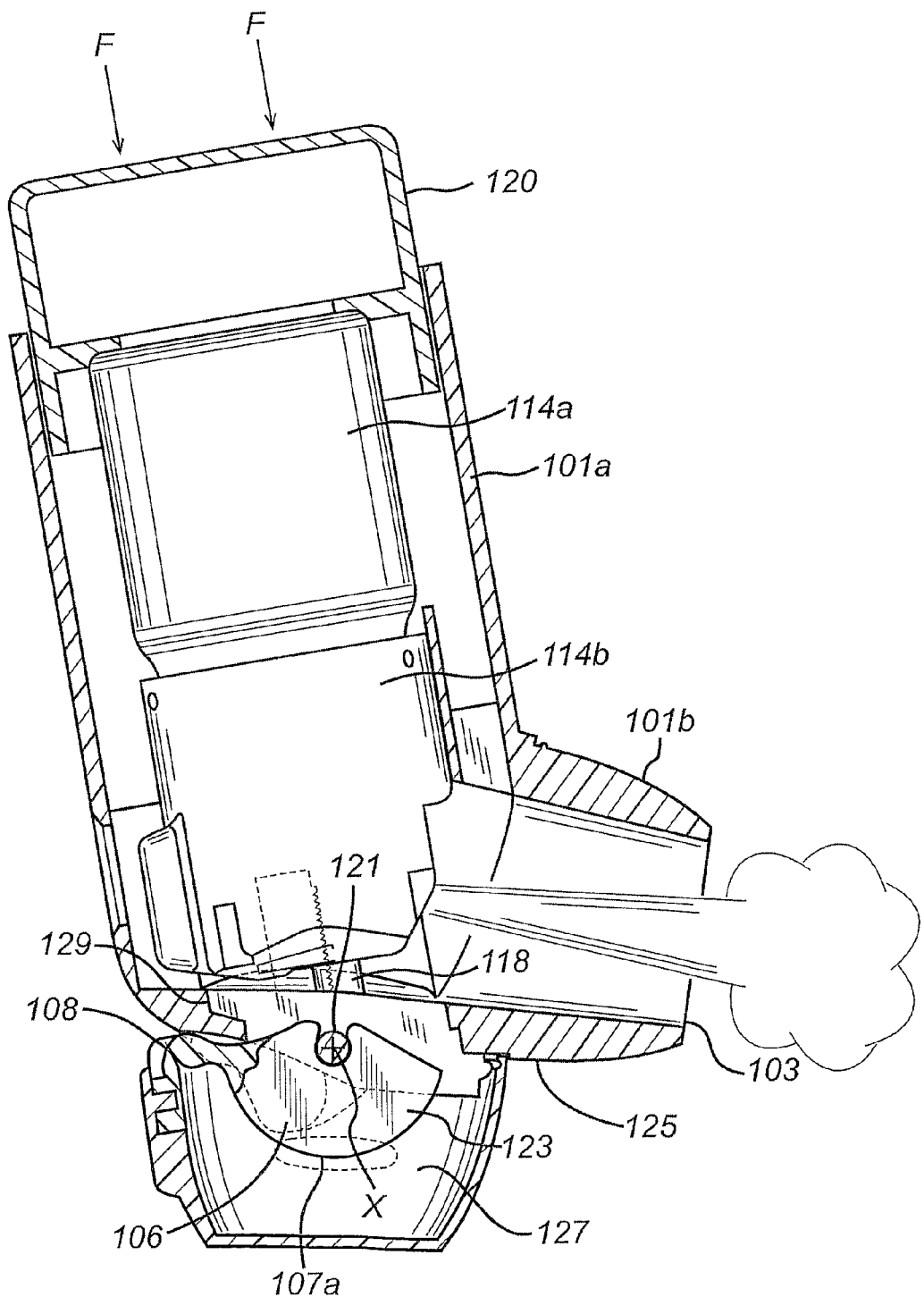
FIG. 13 is a further partial cross-sectional view of the second pMDI with the closure in the open position, secured to a base of the housing, and the restricting surfaces of the associated 'P'-shaped revolvable restricting member having thereby been brought into a position which does not restrict relative movement between the housing and the container unit enabling dispensing of a dose of the medicament formulation.

Referring to the second embodiment in FIG. 13 and the third embodiment in FIG. 15, it will be appreciated that when the closure 105; 205 is in its open position secured to the base 125; 225 of the housing 101; 201, the closure 105; 205 not only encloses the revolvable element 106; 206 and associated slots 129; 229, but also acts as a stand on which the pMDI 170; 270 can be stood upright in its use orientation.

It will be observed that, in the exemplary embodiments of the invention, during movement of the closure from the open to the closed position the container unit is not required to move relative to the housing in order to prevent dispensing of the dose of the medicament formulation. This is different from the inhaler described in UK Patent Application No. 0505543 and counterpart PCT Patent Application PCT/GB2006/000978 in which the revolvable element does not comprise a restricting member and the container unit must be moved relative to the housing in order to bring it into the proximity of a restricting member included in the housing and thereby prevent dispensing of the dose of the medicament formulation.

The exemplary inhalers of the invention are breath-coordinated pMDIs, in distinction from breath-operated pMDIs. An example of a breath-operated pMDI can be seen in U.S. Pat. No. 5,447,150.

The exemplary inhalers of the invention may be used in conjunction with an overwrap package for storing and containing the inhaler, including those described in U.S. Pat. Nos. 6,390,291, 6,119,853, 6,179,118, 6,679,374, 6,315,112, and 6,352,152.

Each of the above-described embodiments may be modified to incorporate one or more features disclosed in U.S. provisional patent application Nos. 60/823,139, 60/823,141, 60/823,134, 60/823,143, 60/823,146, 60/823,151 60/823, 154, all filed on 22 Aug. 2006; and the US patent applications corresponding to International patent application Nos. PCT/GB2006/000963, PCT/GB2006/000966, PCT/GB2006/000978, PCT/GB2006/000978, PCT/GB2006/000975, PCT/GB2006/000965; each of which patent applications is hereby incorporated herein in entirety by reference.

The above-described exemplary embodiments may further be modified to incorporate one or more features from the appended claims.

The medicament contained in the container unit of the present invention may be for the treatment of mild, moderate or severe acute or chronic symptoms or for prophylactic treatment. The medicament is suitable for treating respiratory diseases, e.g. asthma, chronic obstructive pulmonary disease (COPD), although may be for other therapeutic indications, e.g. treating rhinitis.

Appropriate therapeutic agents or medicaments may thus be selected from, for example:

analgesics, e.g., codeine, dihydromorphine, ergotamine, fentanyl or morphine;

anginal preparations, e.g., diltiazem;

antiallergics, e.g., cromoglycate (e.g. as the sodium salt), ketotifen or nedocromil (e.g. as the sodium salt);

antiinfectives e.g., cephalosporins, penicillins, streptomycin, sulphonamides, tetracyclines and pentamidine;

antihistamines, e.g., methapyrilene;

H1 antagonists, e.g., amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine;

H3 antagonists, e.g. those compounds disclosed in WO-A-04035556 and in WO-A-06045416;

H4 antagonists, e.g. the compounds disclosed in Jablonowski et al., *J. Med. Chem.* 46:3957-3960 (2003);

anti-inflammatories, e.g., methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, or ST-126;

antitussives, e.g., noscapine;

bronchodilators, e.g., $\beta_2$-adrenoreceptor agonists including salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol; other β2-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160;

examples of β2-adrenoreceptor agonists include:

3-(4-{[6-({(2R)-2-hydroxy-2-[4-hydroxy-3-(hydroxymethyl)phenyl]ethyl}amino)hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl)amino]-1-hydroxyethyl}-2-(hydroxymethyl)phenol;

4-{(1R)-2-[(6-{4-[3-(cyclopentylsulfonyl)phenyl]butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

PDE4 inhibitors e.g. cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one, cis-[4-cyano-4-(3-cyclopropylmethoxy-4-difluoromethoxyphenyl)cyclohexan-1-ol] and cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference;

further PDE4 inhibitors are disclosed in the published international patent application WO04/024728 (Glaxo Group Ltd), WO04/056823 (Glaxo Group Ltd) and WO04/103998 (Glaxo Group Ltd);

leukotriene antagonists e.g. montelukast, pranlukast and zafirlukast; iNOS inhibitors, e.g. those disclosed in WO-A-9313055, WO-A-9830537, WO-A-0250021, WO-A-9534534 or WO-A-9962875;

adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]; [α4 integrin inhibitors e.g. (2S)-3-[4-({[4-(aminocarbonyl)-1-piperidinyl]carbonyl}oxy)phenyl]-2-[((2S)-4-methyl-2-{[2-(2-ethylphenoxy)acetyl]amino}pentanoyl)amino]propanoic acid (e.g as free acid or potassium salt)];

diuretics, e.g., amiloride;

anticholinergics, e.g., ipratropium (e.g. as bromide) tiotropium, atropine, oxitropium, revatropate (e.g. as the hydrobromide) or LAS-34273 which is disclosed in WO-A-0104118;

hormones, e.g., cortisone, hydrocortisone or prednisolone; xanthines, e.g., aminophylline, choline theophyllinate, lysine theophyllinate or theophylline; # therapeutic proteins and peptides, e.g., insulin or glucagons.

It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

Preferably, the medicament is formulated in a hydrofluoroalkane propellant, such as HFA-134a or HFA-227 or a combination thereof.

Preferably, the medicament is an anti-inflammatory steroid, such as a corticosteroid (for instance fluticasone furoate or fluticasone propionate, mometasone furoate or cyclesonide) or a long acting beta agonist (LABA), such as salmeterol, for example, as the xinafoate salt, or a combination thereof.

Preferred medicaments are salmeterol, salmeterol xinafoate, salbutamol, salbutamol sulphate, fluticasone furoate, fluticasone propionate, mometasone furoate, ciclesonide, and beclomethasone dipropionate and salts, esters or solvates thereof.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicaments may be delivered in combinations. As an example, there may be provided salbutamol (e.g. as the free base of the sulphate salt) or salmeterol (e.g. as the xinafoate salt) in combination with an anti-inflammatory steroid, such as beclomethasone (e.g. as an ester, preferably dipropionate) or fluticasone furoate or fluticasone propionate.

All publications, patents, and patent applications cited herein, whether supra or infra, are hereby incorporated herein by reference to their entirety to the same extent as if each publication, patent, or patent application was specifically and individually indicated to be incorporated by reference.

It must be noted that, as used in the specification and appended claims, the singular forms "a", "an", "the" and "one" include plural referents unless the content clearly dictates otherwise. Also, use of words such as "generally", "about", "approximately", and the like, is meant to include that exact value, property or parameter.

It will be understood that the present invention has been described above by way of example only and that the above description should not be taken to impose any limitation on the scope of the claims. Specifically, although the present invention has been described with reference to a pMDI, the invention is not limited to this form of inhaler. The scope of the invention is defined by the appended claims.

The invention claimed is:

1. An inhaler for use with a container unit containing a medicament formulation to be dispensed, comprising:
    a housing for the container unit and in which the container unit is relatively movable thereto to cause dispensing of a dose of the medicament formulation from the container unit for inhalation by a user through a dispensing outlet of the inhaler;
    a closure movable between a closed position, in which the closure closes the dispensing outlet, and an open position, in which the dispensing outlet is open; and
    a revolvable element comprising a restricting member, the revolvable element in use being revolvable around an axis between a first position, which places the restricting member in a non-restricting position which does not restrict relative movement between the container unit and the housing for dispensing of the dose of the medicament formulation, and a second position, which places the restricting member in a restricting position which does restrict relative movement between the container unit and the housing such that dispensing of the dose of the medicament formulation is prevented;
    wherein the closure is associated with the revolvable element such that movement of the closure from the closed position to the open position causes the revolvable element to move the restricting member from the restricting position to the non-restricting position and vice-versa; and
    wherein a hinge is disposed between the revolvable element and the closure, so that the closure is hingably movable relative to the revolvable element,
    wherein the closure is able to be hinged relative to the revolvable element towards the restricting member, and
    wherein the hinge allows the revolvable element and the closure to be hinged into facing relationship when the closure is in its open position so that the restricting member is covered by the closure.

2. The inhaler of claim 1 wherein the revolvable element revolves around a fixed axis.

3. The inhaler of claim 2 wherein the fixed axis of the revolvable element passes through the inhaler housing.

4. The inhaler of claim 1 wherein during movement of the closure from the open to the closed position the container unit is not required to move relative to the housing in order to prevent dispensing of the dose of the medicament formulation.

5. The inhaler of claim 1 wherein the restricting member has a restricting surface and wherein movement of the closure from the open to the closed position causes the revolvable element to revolve from the first position to the second position and thereby bring the restricting member into its restricting position in which the restricting surface restricts relative movement between the housing and the container unit.

6. The inhaler of claim 5, wherein the restricting surface is a curved surface.

7. The inhaler of claim 6, wherein the curved surface is of constant radius about the axis.

8. The inhaler of claim 5, wherein the revolvable element comprises a generally semi-circular section mounted on the axis and whose circumferential surface forms the restricting surface.

9. The inhaler of claim 1 wherein the axis around which the revolvable element is revolvable passes through the revolvable element.

10. The inhaler of claim 1 wherein the revolvable element is generally 'P'-shaped.

11. The inhaler of claim 10 wherein the axis around which the revolvable element is revolvable passes through the semi-circular part of the 'P'-shape.

12. The inhaler of claim 10, wherein the restricting member has a restricting surface and wherein movement of the closure from the open to the closed position causes the revolvable element to revolve from the first position to the second position and thereby bring the restricting member into its restricting position in which the restricting surface restricts relative movement between the housing and the container unit, and wherein the semicircular surface of the 'P' forms the restricting surface of the restricting member.

13. The inhaler of claim 1, wherein the revolvable element is able to be disposed inside the closure when in its open position.

14. The inhaler of claim 1 wherein the revolvable element and the closure are comprised in a single component part.

15. The inhaler of claim 1 wherein the closure is adapted to be releasably secured to the housing when in the open position.

16. The inhaler of claim 15 wherein the closure is adapted to form a base for the inhaler when secured to the housing.

17. The inhaler of claim 16 wherein the base is adapted to form a stand for the inhaler.

18. The inhaler of claim 1 with the proviso that the inhaler is not a breath-operated inhaler.

19. The inhaler of claim 1 wherein the inhaler is a manually-actuable, breath-coordinated inhaler.

20. The inhaler of claim 1 wherein the inhaler is a pMDI.

21. The inhaler of claim 1, wherein the container unit is a pressurised container unit.

22. The inhaler of claim 1, wherein the container unit comprises a container which contains the medicament formulation.

23. The inhaler of claim 22 in which an accessory is attached to the container.

24. The inhaler of claim 23, wherein the accessory is attached at the leading end of the container.

25. The inhaler of claim 22, wherein the container is a pressurised container.

26. The inhaler of claim 1, wherein the revolvable element consists of the restricting member.

27. The inhaler of claim 1 adapted such that when the closure is in the closed position the restricting member is positioned to abut against the container unit thereby restricting movement of the container unit relative to the housing so as to prevent dispensing of a dose of the medicament formulation and such that when the closure is in the open position the restricting member is positioned so as not to abut against the container unit thereby allowing the container unit to move relative to the housing and allow dispensing of a dose of the medicament formulation.

28. The inhaler of claim 27, wherein the restricting member has a restricting surface and wherein movement of the closure from the open to the closed position causes the revolvable element to revolve from the first position to the second position and thereby bring the restricting member into its restricting position in which the restricting surface restricts relative movement between the housing and the container unit by abutting against the container unit when the closure is in the closed position.

29. The inhaler of claim 27, wherein the restricting member is adapted to abut against an accessory of the container unit when the closure is in its closed position.

30. The inhaler of claim 1 including the container unit in the housing.

31. A closure for use with an inhaler which comprises a housing for receiving therein a container unit containing a medicament formulation and in which the container unit is relatively movable to cause dispensing of a dose of the medicament formulation from the container unit for inhalation by a user through a dispensing outlet of the inhaler;

the closure being adapted to be movably mounted on the inhaler for movement between a closed position, in which the closure closes the dispensing outlet, and an open position, in which the dispensing outlet is open;

the closure comprising a revolvable element comprising a restricting member, the revolvable element being adapted to revolve about an axis on movement of the closure between its closed and open positions, and the revolvable element being placed in first and second positions when the closure is in its open and closed positions respectively;

the first position placing the restricting member in a non-restricting position which does not restrict relative movement between the container unit and the housing for dispensing of the dose of the medicament formulation, and the second position placing the restricting member in a restricting position which does restrict relative movement between the container unit and the housing such that dispensing of the dose of the medicament formulation is prevented;

wherein the closure has a closure part which closes the dispensing outlet, and wherein a hinge is disposed between the revolvable element and the closure part, so that the closure part is hingably movable relative to the revolvable element, wherein the closure part is able to be hinged relative to the revolvable element towards the restricting member, and wherein the hinge allows the revolvable element and the closure part to be hinged into facing relationship so that the restricting member is covered by the closure part.

32. The closure of claim 31 wherein the hinge enables the revolvable element to be disposed in the closure part.

33. The closure of claim 31 wherein the restricting member has a restricting surface and wherein movement of the closure from the open to the closed position causes the revolvable element to revolve from the first position to the second position and thereby bring the restricting member into its restricting position in which the restricting surface restricts relative movement between the housing and the container unit.

34. The closure of claim 31 wherein the axis around which the revolvable element is revolvable passes through the revolvable element.

35. The closure of claim 31 wherein the revolvable element is generally 'P'-shaped.

36. The closure of claim 35 wherein the axis around which the revolvable element is revolvable passes through the semicircular part of the 'P'-shape.

37. The closure of claim 35 wherein the restricting member has a restricting surface, and wherein the semiconductor surface of the 'P' forms the restricting surface of the restricting member.

38. The closure of claim 31 wherein the revolvable element and the closure part are comprised in a single component part that is optionally integrally formed.

39. The closure of claim 1 wherein the revolvable element has a mounting for mounting to an axle of the inhaler for revolving thereabout.

40. The inhaler of claim 14 wherein the revolvable element and the closure are comprised in a single component part that is integrally formed.

41. The inhaler of claim 1 wherein the revolvable element and the closure are connected at the hinge.

42. The inhaler of claim 1 wherein the hinge has a hinge axis about which the closure is hingably movable and the hinge axis is essentially parallel to, but spaced from, the axis about which the revolvable element is revolvable.

43. The inhaler of claim 1 wherein the hinge is such that the relative angle between the closure and the revolvable element is able to change when the revolvable element revolves about the axis.

44. The inhaler of claim 1 wherein the hinge is such that the closure is free to be hinged relative to the revolvable element in a first direction, for moving the closure from the closed position towards the open position whilst the restricting member is in the restricting position, and in a second, opposite direction, for moving the closure over the restricting member when in the non-restricting position.

45. The closure of claim 31 wherein the revolvable element and the closure part are connected at the hinge.

46. The closure of claim 31 wherein the hinge has a hinge axis about which the closure part is hingably movable and the hinge axis is essentially parallel to, but spaced from, the axis about which the revolvable element is revolvable.

47. The closure of claim 31 wherein the hinge is such that the relative angle between the closure part and the revolvable element is able to change when the revolvable element revolves about the axis.

48. The closure of claim 31 wherein the hinge is such that the closure part is free to be hinged relative to the revolvable element in two, opposing directions, one of which moves the closure part over the restricting member.

* * * * *